US011229725B2

(12) United States Patent
Stilwell et al.

(10) Patent No.: US 11,229,725 B2
(45) Date of Patent: *Jan. 25, 2022

(54) CELL REPOPULATED COLLAGEN MATRIX FOR SOFT TISSUE REPAIR AND REGENERATION

(71) Applicant: AlloSource, Centennial, CO (US)

(72) Inventors: Reginald L. Stilwell, Parker, CO (US); Brent Atkinson, Littleton, CO (US); Yaling Shi, Larkspur, CO (US); Brian Dittman, Lenexa, KS (US)

(73) Assignee: ALLOSOURCE, Centennial, CO (US)

( * ) Notice: Subject to any disclaimer, the term of this patent is extended or adjusted under 35 U.S.C. 154(b) by 57 days.

This patent is subject to a terminal disclaimer.

(21) Appl. No.: 16/744,095

(22) Filed: Jan. 15, 2020

(65) Prior Publication Data
US 2020/0179571 A1    Jun. 11, 2020

Related U.S. Application Data

(63) Continuation of application No. 14/938,173, filed on Nov. 11, 2015, now Pat. No. 10,568,990, which is a continuation of application No. 14/207,220, filed on Mar. 12, 2014, now abandoned.

(60) Provisional application No. 61/790,412, filed on Mar. 15, 2013.

(51) Int. Cl.
| | |
|---|---|
| *A61L 27/24* | (2006.01) |
| *A61L 27/60* | (2006.01) |
| *A61K 35/28* | (2015.01) |
| *A61L 27/36* | (2006.01) |
| *A61L 27/38* | (2006.01) |
| *A61L 27/54* | (2006.01) |
| *C12N 5/0775* | (2010.01) |

(52) U.S. Cl.
CPC .............. *A61L 27/60* (2013.01); *A61K 35/28* (2013.01); *A61L 27/24* (2013.01); *A61L 27/362* (2013.01); *A61L 27/3604* (2013.01); *A61L 27/3641* (2013.01); *A61L 27/3687* (2013.01); *A61L 27/3691* (2013.01); *A61L 27/3834* (2013.01); *A61L 27/54* (2013.01); *C12N 5/0667* (2013.01); *A61L 2300/252* (2013.01); *A61L 2300/414* (2013.01); *A61L 2300/426* (2013.01); *A61L 2300/64* (2013.01); *A61L 2430/34* (2013.01); *A61L 2430/40* (2013.01); *C12N 2533/92* (2013.01)

(58) Field of Classification Search
None
See application file for complete search history.

(56) References Cited

U.S. PATENT DOCUMENTS

| | | |
|---|---|---|
| 4,361,552 A | 11/1982 | Baur |
| 4,627,853 A | 12/1986 | Campbell et al. |
| 4,642,120 A | 2/1987 | Itay et al. |
| 4,801,299 A | 1/1989 | Brendel et al. |
| 5,073,373 A | 12/1991 | O'Leary et al. |
| 5,131,850 A | 7/1992 | Brockbank |
| 5,197,985 A | 3/1993 | Caplan et al. |
| 5,284,655 A | 2/1994 | Bogdansky et al. |
| 5,298,254 A | 3/1994 | Prewett et al. |
| 5,306,304 A | 4/1994 | Gendler |
| 5,314,476 A | 5/1994 | Prewett et al. |
| 5,336,616 A | 8/1994 | Livesey et al. |
| 5,405,390 A | 4/1995 | O'Leary et al. |
| 5,439,684 A | 8/1995 | Prewett et al. |
| 5,486,359 A | 1/1996 | Caplan |
| 5,507,813 A | 4/1996 | Dowd et al. |
| 5,510,396 A | 4/1996 | Prewett et al. |
| 5,516,532 A | 5/1996 | Atala et al. |
| 5,531,791 A | 7/1996 | Wolfinbarger |
| 5,556,379 A | 9/1996 | Wolfinbarger |
| 5,676,146 A | 10/1997 | Scarborough |
| 5,707,962 A | 1/1998 | Chen et al. |
| 5,723,010 A | 3/1998 | Yui et al. |
| 5,736,396 A | 4/1998 | Bruder et al. |
| 5,749,874 A | 5/1998 | Schwartz |
| 5,769,899 A | 6/1998 | Schwartz et al. |
| 5,786,207 A | 7/1998 | Katz et al. |
| 5,788,941 A | 8/1998 | Dalmasso et al. |
| 5,797,871 A | 8/1998 | Wolfinbarger |
| 5,811,094 A | 9/1998 | Caplan |

(Continued)

FOREIGN PATENT DOCUMENTS

| | | |
|---|---|---|
| EP | 2 954 044 | 11/2015 |
| EP | 2 970 882 | 1/2016 |

(Continued)

OTHER PUBLICATIONS

Adkisson, H.D., et al., "The Potential of Human Allogeneic Juvenile Chondrocytes for Restoration of Articular Cartilage", American Journal of Sports Medicine., vol. 38, No. 7, pp. 1324-1333, Apr. 27, 2010.
Ahn, et al., "In Vivo Osteogenic Differentiation of Human Adipose-Derived Stem Cells in an Injectable in Situ-Forming D Gel Scaffold", Tissue Eng Part A, vol. 15, No. 7, pp. 1821-1832, (2009).
Albrecht, F., et al. "Closure of Osteochondral Lesions Using Chondral Fragments and Fibrin Adhesive." Archives of Orthopaedic and Traumatic Surgery, vol. 101, pp. 213-217, (1983).

(Continued)

*Primary Examiner* — Scott Long
*Assistant Examiner* — Evelyn Y Pyla
(74) *Attorney, Agent, or Firm* — Kilpatrick, Townsend & Stockton LLP

(57) ABSTRACT

The present invention provides compositions for treating soft tissue injuries comprising a collagen matrix and mesenchymal stem cells adhered to the collagen matrix. Methods of making and using compositions comprising a collagen matrix and mesenchymal stem cells adhered to the collagen matrix are also provided.

15 Claims, 5 Drawing Sheets

(56) References Cited

U.S. PATENT DOCUMENTS

| | | |
|---|---|---|
| 5,820,581 A | 10/1998 | Wolfinbarger |
| 5,827,740 A | 10/1998 | Pittenger |
| 5,837,278 A | 11/1998 | Geistlich et al. |
| 5,876,451 A | 3/1999 | Yui et al. |
| 5,895,426 A | 4/1999 | Scarborough et al. |
| 5,899,939 A | 5/1999 | Boyce et al. |
| 5,906,934 A | 5/1999 | Grande et al. |
| 5,908,782 A | 6/1999 | Marshak et al. |
| 5,908,784 A | 6/1999 | Johnstone et al. |
| 5,942,225 A | 8/1999 | Bruder et al. |
| 5,948,428 A | 9/1999 | Lee et al. |
| 5,962,325 A | 10/1999 | Naughton et al. |
| 5,972,368 A | 10/1999 | McKay |
| 5,976,104 A | 11/1999 | Wolfinbarger |
| 5,977,034 A | 11/1999 | Wolfinbarger |
| 5,977,432 A | 11/1999 | Wolfinbarger |
| 5,989,498 A | 11/1999 | Odland |
| 5,993,844 A | 11/1999 | Abraham et al. |
| 6,022,540 A | 2/2000 | Bruder et al. |
| 6,024,735 A | 2/2000 | Wolfinbarger |
| 6,030,635 A | 2/2000 | Gertzman et al. |
| 6,030,836 A | 2/2000 | Thiede |
| 6,050,991 A | 4/2000 | Guillet |
| 6,063,094 A | 5/2000 | Rosenberg |
| 6,090,998 A | 7/2000 | Grooms et al. |
| 6,143,012 A | 11/2000 | Gausepohl |
| 6,152,142 A | 11/2000 | Tseng |
| 6,174,333 B1 | 1/2001 | Kadiyala |
| 6,180,606 B1 | 1/2001 | Chen et al. |
| 6,189,537 B1 | 2/2001 | Wolfinbarger |
| 6,200,347 B1 | 3/2001 | Anderson et al. |
| 6,200,606 B1 | 3/2001 | Peterson |
| 6,203,755 B1 | 3/2001 | Odland |
| 6,214,369 B1 | 4/2001 | Grande |
| 6,225,119 B1 | 5/2001 | Qasba et al. |
| 6,235,316 B1 | 5/2001 | Adkisson |
| 6,280,437 B1 | 8/2001 | Pacala et al. |
| 6,291,240 B1 | 9/2001 | Mansbridge et al. |
| 6,294,041 B1 | 9/2001 | Boyce et al. |
| 6,294,187 B1 | 9/2001 | Boyce et al. |
| 6,305,379 B1 | 10/2001 | Wolfinbarger |
| 6,315,795 B1 | 11/2001 | Scarborough et al. |
| 6,322,784 B1 | 11/2001 | Pittenger et al. |
| 6,326,018 B1 | 12/2001 | Gertzman et al. |
| 6,326,019 B1 | 12/2001 | Tseng |
| 6,340,477 B1 | 1/2002 | Anderson |
| 6,355,239 B1 | 3/2002 | Bruder |
| 6,371,988 B1 | 4/2002 | Pafford et al. |
| 6,379,953 B1 | 4/2002 | Bruder et al. |
| 6,387,367 B1 | 5/2002 | Davis-Sproul et al. |
| 6,391,297 B1 | 5/2002 | Halvorsen |
| 6,432,710 B1 | 8/2002 | Boss |
| 6,436,138 B1 | 8/2002 | Dowd |
| 6,464,983 B1 | 10/2002 | Grotendorst |
| 6,478,825 B1 | 11/2002 | Winterbottom et al. |
| 6,482,231 B1 | 11/2002 | Abatangelo |
| 6,482,233 B1 | 11/2002 | Aebi et al. |
| 6,511,509 B1 | 1/2003 | Ford et al. |
| 6,514,514 B1 | 2/2003 | Atkinson et al. |
| 6,534,095 B1 | 3/2003 | Moore-Smith et al. |
| 6,541,024 B1 | 4/2003 | Kadiyala et al. |
| 6,555,374 B1 | 4/2003 | Gimble et al. |
| 6,576,015 B2 | 6/2003 | Geistlich et al. |
| 6,576,265 B1 | 6/2003 | Spievack |
| 6,593,138 B1 | 7/2003 | Oliver et al. |
| 6,607,524 B1 | 8/2003 | LaBudde et al. |
| 6,616,698 B2 | 9/2003 | Scarborough |
| 6,626,945 B2 | 9/2003 | Simon et al. |
| 6,638,271 B2 | 10/2003 | Munnerlyn et al. |
| 6,645,764 B1 | 11/2003 | Adkisson |
| 6,652,593 B2 | 11/2003 | Boyer, II et al. |
| 6,652,594 B2 | 11/2003 | Francis et al. |
| 6,670,269 B2 | 12/2003 | Mashino |
| 6,685,626 B2 | 2/2004 | Wironen |
| 6,696,073 B2 | 2/2004 | Boyce et al. |
| 6,712,822 B2 | 3/2004 | Re et al. |
| 6,716,245 B2 | 4/2004 | Pasquet et al. |
| 6,746,484 B1 | 6/2004 | Liu et al. |
| 6,777,231 B1 | 8/2004 | Katz |
| 6,800,480 B1 | 10/2004 | Bodnar et al. |
| 6,805,713 B1 | 10/2004 | Carter et al. |
| 6,808,585 B2 | 10/2004 | Boyce et al. |
| 6,830,149 B2 | 12/2004 | Merboth et al. |
| 6,835,377 B2 | 12/2004 | Goldberg et al. |
| 6,837,907 B2 | 1/2005 | Wolfinbarger |
| 6,849,273 B2 | 2/2005 | Spievack |
| 6,855,169 B2 | 2/2005 | Boyer et al. |
| 6,858,042 B2 | 2/2005 | Nadler et al. |
| 6,863,694 B1 | 3/2005 | Boyce et al. |
| 6,863,900 B2 | 3/2005 | Kadiyala |
| 6,902,578 B1 | 6/2005 | Anderson et al. |
| 6,911,045 B2 | 6/2005 | Shimp |
| 6,911,212 B2 | 6/2005 | Gertzman et al. |
| 6,989,030 B1 | 1/2006 | Ohgushi |
| 6,998,135 B1 | 2/2006 | Sunwoo et al. |
| 7,018,412 B2 | 3/2006 | Ferreira et al. |
| 7,029,666 B2 | 4/2006 | Bruder et al. |
| 7,048,765 B1 | 5/2006 | Grooms et al. |
| 7,067,123 B2 | 6/2006 | Gomes et al. |
| 7,115,146 B2 | 10/2006 | Boyer, II et al. |
| 7,132,110 B2 | 11/2006 | Kay et al. |
| 7,144,588 B2 | 12/2006 | Oray et al. |
| 7,153,500 B2 | 12/2006 | Qasba et al. |
| 7,163,691 B2 | 1/2007 | Knaack et al. |
| 7,172,629 B2 | 2/2007 | McKay |
| 7,179,649 B2 | 2/2007 | Halvorsen |
| 7,229,440 B2 | 6/2007 | Alden et al. |
| 7,241,874 B2 | 7/2007 | Thome |
| 7,259,011 B2 | 8/2007 | Lucas |
| 7,288,086 B1 | 10/2007 | Manvel et al. |
| 7,291,450 B2 | 11/2007 | Sowemimo-Coker et al. |
| 7,297,540 B2 | 11/2007 | Mitrani |
| 7,316,822 B2 | 1/2008 | Binette et al. |
| 7,323,011 B2 | 1/2008 | Shepard et al. |
| 7,335,381 B2 | 2/2008 | Malinin |
| 7,338,495 B2 | 3/2008 | Adams |
| 7,338,517 B2 | 3/2008 | Yost et al. |
| 7,338,757 B2 | 3/2008 | Wolfinbarger, Jr. et al. |
| 7,347,876 B2 | 3/2008 | Tsai |
| 7,351,241 B2 | 4/2008 | Bendett et al. |
| 7,361,195 B2 | 4/2008 | Schwartz et al. |
| 7,371,409 B2 | 5/2008 | Petersen et al. |
| 7,393,437 B2 | 7/2008 | Chan |
| 7,470,537 B2 | 12/2008 | Hendrick et al. |
| 7,473,420 B2 | 1/2009 | Fraser et al. |
| 7,494,802 B2 | 2/2009 | Tseng |
| 7,498,040 B2 | 3/2009 | Masinaei et al. |
| 7,501,115 B2 | 3/2009 | Fraser et al. |
| 7,582,309 B2 | 9/2009 | Rosenberg et al. |
| 7,595,043 B2 | 9/2009 | Hedrick et al. |
| 7,595,377 B2 | 9/2009 | Stone |
| 7,608,113 B2 | 10/2009 | Boyer et al. |
| 7,622,562 B2 | 11/2009 | Thorne et al. |
| 7,625,581 B2 | 12/2009 | Laredo et al. |
| 7,662,185 B2 | 2/2010 | Alfaro et al. |
| 7,662,625 B2 | 2/2010 | Stern et al. |
| 7,687,059 B2 | 3/2010 | Fraser et al. |
| RE41,286 E | 4/2010 | Atkinson et al. |
| 7,723,108 B2 | 5/2010 | Truncale et al. |
| 7,727,550 B2 | 6/2010 | Siegal et al. |
| 7,732,126 B2 | 6/2010 | Zhang et al. |
| 7,753,963 B2 | 7/2010 | Boyer et al. |
| 7,754,232 B2 | 7/2010 | Fisher et al. |
| 7,763,071 B2 | 7/2010 | Bianchi et al. |
| 7,775,965 B2 | 8/2010 | McFetridge |
| 7,776,089 B2 | 8/2010 | Bianchi et al. |
| 7,785,634 B2 | 8/2010 | Borden |
| 7,807,458 B2 | 10/2010 | Schiller |
| 7,811,608 B2 | 10/2010 | Kay et al. |
| 7,815,926 B2 | 10/2010 | Syring et al. |
| 7,824,671 B2 | 11/2010 | Binder |
| 7,824,711 B2 | 11/2010 | Kizer et al. |
| 7,837,740 B2 | 11/2010 | Semler et al. |
| 7,863,043 B2 | 1/2011 | Gentry et al. |

(56) References Cited

U.S. PATENT DOCUMENTS

| | | |
|---|---|---|
| 7,875,296 B2 | 1/2011 | Binette et al. |
| 7,879,103 B2 | 2/2011 | Gertzman et al. |
| 7,883,511 B2 | 2/2011 | Femyhough |
| RE42,208 E | 3/2011 | Truncale et al. |
| 7,902,145 B2 | 3/2011 | Chu |
| 7,914,779 B2 | 3/2011 | Hariri |
| 7,928,280 B2 | 4/2011 | Hariri et al. |
| 7,931,692 B2 | 4/2011 | Sybert et al. |
| 8,002,813 B2 | 8/2011 | Scarborough et al. |
| 8,002,837 B2 | 8/2011 | Stream et al. |
| 8,021,692 B2 | 9/2011 | Hiles |
| 8,025,896 B2 | 9/2011 | Malaviya et al. |
| 8,039,016 B2 | 10/2011 | Drapeau et al. |
| 8,043,450 B2 | 10/2011 | Cali et al. |
| 8,058,066 B2 | 11/2011 | Marshall |
| 8,071,135 B2 | 12/2011 | Liu et al. |
| 8,074,661 B2 | 12/2011 | Hutson et al. |
| 8,105,634 B2 | 1/2012 | Liu et al. |
| RE43,258 E | 3/2012 | Truncale et al. |
| 8,133,421 B2 | 3/2012 | Boyce et al. |
| 8,137,702 B2 | 3/2012 | Binette et al. |
| 8,142,502 B2 | 3/2012 | Stone et al. |
| 8,153,162 B2 | 4/2012 | Tseng |
| 8,158,141 B2 | 4/2012 | Chen |
| 8,163,549 B2 | 4/2012 | Yao et al. |
| 8,167,943 B2 | 5/2012 | Carter et al. |
| 8,171,937 B2 | 5/2012 | Bendett et al. |
| 8,173,162 B2 | 5/2012 | Vilei et al. |
| 8,182,840 B2 | 5/2012 | Tseng |
| 8,182,841 B2 | 5/2012 | Tseng |
| 8,187,639 B2 | 5/2012 | Tseng |
| 8,197,474 B2 | 6/2012 | Scarborough et al. |
| 8,198,245 B2 | 6/2012 | Niklason |
| 8,202,539 B2 | 6/2012 | Behnam et al. |
| 8,221,500 B2 | 7/2012 | Truncale et al. |
| 8,231,908 B2 | 7/2012 | Kinoshita |
| 8,268,008 B2 | 9/2012 | Betz et al. |
| 8,292,968 B2 | 10/2012 | Truncale et al. |
| 8,309,106 B2 | 11/2012 | Masinaei et al. |
| 8,318,212 B2 | 11/2012 | Malinin |
| 8,323,701 B2 | 12/2012 | Daniel et al. |
| 8,328,876 B2 | 12/2012 | Behnam et al. |
| 8,334,135 B2 | 12/2012 | Rodriguez et al. |
| 8,343,229 B2 | 1/2013 | Coale |
| 8,357,384 B2 | 1/2013 | Behnam et al. |
| 8,357,403 B2 | 1/2013 | Daniel et al. |
| 8,372,437 B2 | 2/2013 | Daniel |
| 8,372,438 B2 | 2/2013 | Daniel et al. |
| 8,372,439 B2 | 2/2013 | Daniel et al. |
| 8,389,017 B1 | 3/2013 | Starling et al. |
| 8,399,010 B2 | 3/2013 | McKay |
| 8,403,991 B2 | 3/2013 | Ullrich, Jr. et al. |
| 8,409,623 B2 | 4/2013 | Shim et al. |
| 8,409,626 B2 | 4/2013 | Daniel |
| 8,420,126 B2 | 4/2013 | Tseng |
| 8,435,551 B2 | 5/2013 | Semler et al. |
| 8,435,566 B2 | 5/2013 | Behnam et al. |
| 8,440,235 B2 | 5/2013 | Tseng |
| 8,455,009 B2 | 6/2013 | Tseng et al. |
| 8,460,714 B2 | 6/2013 | Tseng et al. |
| 8,480,757 B2 | 7/2013 | Gage et al. |
| 8,496,970 B2 | 7/2013 | Binette et al. |
| 8,497,121 B2 | 7/2013 | Yao et al. |
| 8,506,632 B2 | 8/2013 | Ganem et al. |
| 8,518,433 B2 | 8/2013 | Kizer et al. |
| 8,524,268 B2 | 9/2013 | Kizer et al. |
| 8,551,176 B2 | 10/2013 | Ullrich, Jr. et al. |
| 8,563,040 B2 | 10/2013 | Marchosky |
| 8,574,825 B2 | 11/2013 | Shelby et al. |
| 8,585,766 B2 | 11/2013 | Ullrich, Jr. et al. |
| 8,637,004 B2 | 1/2014 | Danilkovich et al. |
| 8,641,775 B2 | 2/2014 | Harmon et al. |
| 8,642,092 B2 | 2/2014 | Daniel et al. |
| 8,652,214 B2 | 2/2014 | Fritz et al. |
| 8,652,458 B2 | 2/2014 | Jackson et al. |
| 8,652,507 B2 | 2/2014 | Kizer et al. |
| 8,703,206 B2 | 4/2014 | Daniel et al. |
| 8,703,207 B2 | 4/2014 | Daniel et al. |
| 8,709,493 B2 | 4/2014 | Daniel et al. |
| 8,709,494 B2 | 4/2014 | Daniel |
| 8,722,075 B2 | 5/2014 | Shimp et al. |
| 8,734,525 B2 | 5/2014 | Behnam et al. |
| 8,758,791 B2 | 6/2014 | McKay |
| 8,771,368 B2 | 7/2014 | McKay |
| 8,822,415 B2 | 9/2014 | Trumpower et al. |
| 8,834,928 B1 | 9/2014 | Truncale et al. |
| 8,859,007 B2 | 10/2014 | Carter et al. |
| 8,865,199 B2 | 10/2014 | Coleman et al. |
| 8,883,210 B1 | 11/2014 | Truncale et al. |
| 8,945,535 B2 | 2/2015 | Steinwachs et al. |
| 8,992,964 B2 | 3/2015 | Shelby et al. |
| 9,005,646 B2 | 4/2015 | Masinaei et al. |
| 9,029,077 B2 | 5/2015 | Song et al. |
| 9,050,178 B2 | 6/2015 | Barry et al. |
| 9,084,767 B2 | 7/2015 | Daniel et al. |
| 9,095,524 B2 | 8/2015 | Warnke et al. |
| 9,162,012 B2 | 10/2015 | Benham et al. |
| 9,180,166 B2 | 11/2015 | Arinzeh et al. |
| 9,186,382 B2 | 11/2015 | Daniel et al. |
| 9,192,695 B2 | 11/2015 | Shi |
| 9,193,948 B2 | 11/2015 | Nicoll et al. |
| 9,265,800 B2 | 2/2016 | Daniel |
| 9,265,801 B2 | 2/2016 | Daniel |
| 9,272,003 B2 | 3/2016 | Daniel et al. |
| 9,272,005 B2 | 3/2016 | Daniel |
| 9,408,875 B2 | 8/2016 | Masinaei et al. |
| 10,568,990 B2 | 2/2020 | Stilwell et al. |
| 2002/0192263 A1 | 12/2002 | Merboth et al. |
| 2003/0050709 A1 | 3/2003 | Noth et al. |
| 2003/0055502 A1 | 3/2003 | Lang et al. |
| 2003/0161817 A1 | 8/2003 | Young et al. |
| 2004/0048796 A1 | 3/2004 | Hariri |
| 2004/0078090 A1 | 4/2004 | Binette et al. |
| 2004/0260315 A1 | 12/2004 | Dell et al. |
| 2005/0019865 A1 | 1/2005 | Kihm |
| 2005/0048036 A1 | 3/2005 | Hedrick et al. |
| 2005/0058631 A1 | 3/2005 | Kihm |
| 2005/0100876 A1 | 5/2005 | Khirabadi et al. |
| 2005/0186286 A1 | 8/2005 | Takami |
| 2005/0288796 A1 | 12/2005 | Awad et al. |
| 2006/0134781 A1 | 6/2006 | Yang et al. |
| 2006/0210643 A1 | 9/2006 | Truncale et al. |
| 2006/0234376 A1 | 10/2006 | Mistry |
| 2007/0077237 A1 | 4/2007 | Damari et al. |
| 2007/0134216 A1 | 6/2007 | Harlow et al. |
| 2007/0160588 A1 | 7/2007 | Kihm |
| 2007/0179607 A1 | 8/2007 | Hodorek et al. |
| 2007/0185231 A1 | 8/2007 | Liu et al. |
| 2007/0212676 A1 | 9/2007 | Takakura |
| 2007/0249044 A1 | 10/2007 | Desai et al. |
| 2007/0258963 A1 | 11/2007 | Danilkovitch et al. |
| 2007/0260109 A1* | 11/2007 | Squillace ............ A61L 27/3687 600/36 |
| 2007/0265705 A1 | 11/2007 | Gaissmaier et al. |
| 2008/0046095 A1 | 2/2008 | Daniel |
| 2008/0058953 A1 | 3/2008 | Scarborough |
| 2008/0160496 A1 | 7/2008 | Rzepakovsky et al. |
| 2008/0195216 A1 | 8/2008 | Phillip |
| 2008/0249632 A1 | 10/2008 | Stone et al. |
| 2008/0249638 A1 | 10/2008 | Asgari |
| 2008/0269895 A1 | 10/2008 | Steinwachs et al. |
| 2008/0305145 A1 | 12/2008 | Shelby et al. |
| 2009/0024223 A1 | 1/2009 | Chen et al. |
| 2009/0041730 A1 | 2/2009 | Barry et al. |
| 2009/0258082 A1 | 10/2009 | Nikaido et al. |
| 2009/0312842 A1 | 12/2009 | Bursac et al. |
| 2010/0049322 A1 | 2/2010 | McKay |
| 2010/0112543 A1 | 5/2010 | Ngo |
| 2010/0124776 A1 | 5/2010 | Shi |
| 2010/0168869 A1 | 7/2010 | Long et al. |
| 2010/0196333 A1 | 8/2010 | Gaskins et al. |
| 2010/0196478 A1 | 8/2010 | Masters |
| 2010/0211173 A1 | 8/2010 | Bárdos et al. |
| 2010/0241228 A1 | 9/2010 | Syring et al. |

(56) References Cited

U.S. PATENT DOCUMENTS

| | | |
|---|---|---|
| 2010/0247494 A1 | 9/2010 | Gregory et al. |
| 2010/0266559 A1 | 10/2010 | Nataraj et al. |
| 2010/0291172 A1 | 11/2010 | Drunecky |
| 2010/0304487 A1 | 12/2010 | Truncale |
| 2011/0045044 A1 | 2/2011 | Masinaei et al. |
| 2011/0070271 A1 | 3/2011 | Truncale et al. |
| 2011/0091434 A1 | 4/2011 | Miller |
| 2011/0104100 A1 | 5/2011 | Riordan |
| 2011/0160857 A1 | 6/2011 | Bracone |
| 2011/0182961 A1 | 7/2011 | McKay |
| 2011/0183001 A1 | 7/2011 | Rosson et al. |
| 2011/0196355 A1 | 8/2011 | Mitchell et al. |
| 2011/0206776 A1 | 8/2011 | Tom et al. |
| 2011/0256202 A1 | 10/2011 | Tom et al. |
| 2011/0262393 A1 | 10/2011 | Yang |
| 2011/0262404 A1 | 10/2011 | Badoer et al. |
| 2011/0262516 A1 | 10/2011 | Zheng et al. |
| 2011/0274729 A1 | 11/2011 | Collins |
| 2011/0293577 A1 | 12/2011 | Vesey |
| 2011/0311496 A1 | 12/2011 | Pittenger et al. |
| 2011/0318314 A1 | 12/2011 | Aggarwal et al. |
| 2012/0009644 A1 | 1/2012 | Hanby et al. |
| 2012/0009679 A1 | 1/2012 | Hanby et al. |
| 2012/0010725 A1 | 1/2012 | Hanby et al. |
| 2012/0063997 A1 | 3/2012 | Hunter |
| 2012/0078378 A1 | 3/2012 | Daniel et al. |
| 2012/0082704 A1 | 4/2012 | Phillips et al. |
| 2012/0083900 A1 | 4/2012 | Samaniego et al. |
| 2012/0087958 A1 | 4/2012 | Dufrane et al. |
| 2012/0128641 A1 | 5/2012 | Austen |
| 2012/0141595 A1 | 6/2012 | Tseng et al. |
| 2012/0142102 A1 | 6/2012 | Chen |
| 2012/0148537 A1 | 6/2012 | Chan et al. |
| 2012/0148548 A1 | 6/2012 | Barry et al. |
| 2012/0158134 A1 | 6/2012 | Codori-Hurff et al. |
| 2012/0164114 A1 | 6/2012 | Abbot |
| 2012/0189583 A1 | 7/2012 | Liu et al. |
| 2012/0189586 A1 | 7/2012 | Harrell |
| 2012/0191184 A1 | 7/2012 | Chen |
| 2012/0201787 A1 | 8/2012 | Abbot |
| 2012/0213859 A1 | 8/2012 | Shelby et al. |
| 2012/0215208 A1 | 8/2012 | Bendett et al. |
| 2012/0221118 A1 | 8/2012 | Bartee et al. |
| 2012/0225484 A1 | 9/2012 | Bhatia et al. |
| 2012/0251609 A1 | 10/2012 | Huang et al. |
| 2012/0263763 A1 | 10/2012 | Sun et al. |
| 2012/0264211 A1 | 10/2012 | Jomha et al. |
| 2012/0269774 A1 | 10/2012 | Ichim |
| 2012/0276080 A1 | 11/2012 | Kinoshita et al. |
| 2012/0294810 A1 | 11/2012 | Daniel |
| 2012/0294811 A1 | 11/2012 | Daniel |
| 2012/0294908 A1 | 11/2012 | Daniel et al. |
| 2012/0294910 A1 | 11/2012 | Daniel et al. |
| 2012/0308529 A1 | 12/2012 | Zanotti et al. |
| 2012/0328690 A1 | 12/2012 | Tseng et al. |
| 2012/0330423 A1 | 12/2012 | Lin et al. |
| 2013/0004464 A1 | 1/2013 | Nadal-Ginard |
| 2013/0004465 A1 | 1/2013 | Aberman |
| 2013/0006385 A1 | 1/2013 | Daniel |
| 2013/0035676 A1 | 2/2013 | Mitchell et al. |
| 2013/0052169 A1 | 2/2013 | Marom |
| 2013/0209572 A1 | 3/2013 | Wilhelmi et al. |
| 2013/0103061 A1 | 4/2013 | Harper |
| 2013/0108670 A1 | 5/2013 | Lynch et al. |
| 2013/0121970 A1 | 5/2013 | Owens et al. |
| 2013/0122095 A1 | 5/2013 | Kestler et al. |
| 2013/0131804 A1 | 5/2013 | Barry et al. |
| 2013/0149294 A1 | 6/2013 | Rueger et al. |
| 2013/0189338 A1 | 7/2013 | Drapeau et al. |
| 2013/0190729 A1* | 7/2013 | Izadpanah ............ C12N 15/88 604/522 |
| 2013/0190893 A1 | 7/2013 | Roock et al. |
| 2013/0195809 A1 | 8/2013 | Crawford et al. |
| 2013/0195810 A1 | 8/2013 | Crawford et al. |
| 2013/0197654 A1 | 8/2013 | Samuelson et al. |
| 2013/0202676 A1 | 8/2013 | Koob et al. |
| 2013/0204392 A1 | 8/2013 | Law et al. |
| 2013/0218274 A1 | 8/2013 | Spencer et al. |
| 2013/0230561 A1 | 9/2013 | Daniel et al. |
| 2013/0287741 A1 | 10/2013 | Reginald et al. |
| 2013/0316454 A1 | 11/2013 | Lu et al. |
| 2013/0344114 A1 | 12/2013 | Chang et al. |
| 2013/0344162 A1 | 12/2013 | Morse et al. |
| 2014/0012393 A1 | 1/2014 | Shin et al. |
| 2014/0017280 A1 | 1/2014 | Daniel et al. |
| 2014/0017283 A1 | 1/2014 | Yoo et al. |
| 2014/0017292 A1 | 1/2014 | Yoo et al. |
| 2014/0024115 A1 | 1/2014 | Bogdansky et al. |
| 2014/0030309 A1 | 1/2014 | Yoo et al. |
| 2014/0037598 A1 | 2/2014 | Jansen et al. |
| 2014/0039621 A1 | 2/2014 | Gordon et al. |
| 2014/0050788 A1 | 2/2014 | Daniel et al. |
| 2014/0052247 A1 | 2/2014 | Daniel et al. |
| 2014/0052274 A1 | 2/2014 | Koob et al. |
| 2014/0058527 A1 | 2/2014 | Truncale et al. |
| 2014/0093543 A1 | 4/2014 | Morreale |
| 2014/0105872 A1 | 4/2014 | Danilkovich et al. |
| 2014/0106447 A1 | 4/2014 | Brown et al. |
| 2014/0112894 A1 | 4/2014 | Zheng et al. |
| 2014/0121772 A1 | 5/2014 | Emerton et al. |
| 2014/0127177 A1 | 5/2014 | Tom et al. |
| 2014/0127317 A1 | 5/2014 | Jansen et al. |
| 2014/0140964 A1 | 5/2014 | Brown et al. |
| 2014/0140966 A1 | 5/2014 | Tom et al. |
| 2014/0161776 A1 | 6/2014 | Aggarwal et al. |
| 2014/0170232 A1 | 6/2014 | Shelby et al. |
| 2014/0205646 A1 | 7/2014 | Morse et al. |
| 2014/0205674 A1 | 7/2014 | Wei |
| 2014/0208980 A1 | 7/2014 | Song et al. |
| 2014/0212471 A1 | 7/2014 | Drapeau et al. |
| 2014/0212499 A1 | 7/2014 | Cooper et al. |
| 2014/0214176 A1 | 7/2014 | Daniel et al. |
| 2014/0220142 A1 | 8/2014 | Song et al. |
| 2014/0222159 A1 | 8/2014 | Bursac et al. |
| 2014/0227339 A1 | 8/2014 | Jackson et al. |
| 2014/0234272 A1 | 8/2014 | Vesey et al. |
| 2014/0234387 A1 | 8/2014 | Daniel et al. |
| 2014/0255356 A1 | 9/2014 | Victor et al. |
| 2014/0255496 A1 | 9/2014 | Daniel et al. |
| 2014/0255506 A1 | 9/2014 | Behnam et al. |
| 2014/0255508 A1 | 9/2014 | Morse et al. |
| 2014/0277570 A1 | 9/2014 | Behnam et al. |
| 2014/0286911 A1 | 9/2014 | Shi et al. |
| 2014/0294777 A1 | 10/2014 | Tom et al. |
| 2014/0301986 A1 | 10/2014 | Tom et al. |
| 2014/0302162 A1 | 10/2014 | Morse et al. |
| 2014/0314822 A1 | 10/2014 | Carter et al. |
| 2014/0342013 A1 | 11/2014 | He et al. |
| 2014/0343688 A1 | 11/2014 | Morse et al. |
| 2015/0004211 A1 | 1/2015 | Yoo et al. |
| 2015/0004247 A1 | 1/2015 | Carter et al. |
| 2015/0010506 A1 | 1/2015 | Jansen et al. |
| 2015/0010609 A1 | 1/2015 | Tom et al. |
| 2015/0010610 A1 | 1/2015 | Tom et al. |
| 2015/0012107 A1 | 1/2015 | Koford et al. |
| 2015/0017222 A1 | 1/2015 | Yoo et al. |
| 2015/0030571 A1 | 1/2015 | Tremolada |
| 2015/0037387 A1 | 2/2015 | Coleman et al. |
| 2015/0093429 A1 | 4/2015 | Carter et al. |
| 2015/0140057 A1 | 5/2015 | Yoo et al. |
| 2015/0140114 A1 | 5/2015 | Sasko |
| 2015/0174295 A1 | 6/2015 | Woodell-May et al. |
| 2015/0174297 A1 | 6/2015 | Daniel |
| 2015/0182667 A1 | 6/2015 | Daniel |
| 2015/0182667 A1 | 7/2015 | Guelcher et al. |
| 2015/0202345 A1 | 7/2015 | Shelby et al. |
| 2015/0202346 A1 | 7/2015 | Shelby et al. |
| 2015/0251361 A1 | 9/2015 | Meyer et al. |
| 2015/0258244 A1 | 9/2015 | Shelby et al. |
| 2015/0265747 A1 | 9/2015 | Daniel |
| 2015/0306278 A1 | 10/2015 | McKay |
| 2016/0030639 A1 | 2/2016 | Shi |

(56) References Cited

U.S. PATENT DOCUMENTS

| | | |
|---|---|---|
| 2016/0045640 A1 | 2/2016 | Shi |
| 2016/0067377 A1 | 3/2016 | Shi et al. |
| 2016/0263284 A1 | 9/2016 | Shi |

FOREIGN PATENT DOCUMENTS

| | | |
|---|---|---|
| WO | 1997026326 | 7/1997 |
| WO | 2002000272 A2 | 1/2002 |
| WO | 2005058207 | 6/2005 |
| WO | 2006062989 A1 | 12/2005 |
| WO | 2006112390 A1 | 10/2006 |
| WO | 2008036374 A1 | 2/2008 |
| WO | 2008041854 A1 | 4/2008 |
| WO | 2010059565 | 5/2010 |
| WO | 2010059783 A2 | 5/2010 |
| WO | 2012083021 A1 | 6/2012 |
| WO | 2012083023 A1 | 6/2012 |
| WO | 2012088396 A2 | 6/2012 |
| WO | 2012112410 | 8/2012 |
| WO | 2012112417 | 8/2012 |
| WO | 2012112441 | 8/2012 |
| WO | 2012116372 A1 | 8/2012 |
| WO | 2012135205 | 8/2012 |
| WO | 2012136701 A1 | 10/2012 |
| WO | 2012170905 A1 | 10/2012 |
| WO | 2013032938 A1 | 12/2012 |
| WO | 2013047936 | 3/2013 |
| WO | 2014151091 A2 | 9/2014 |
| WO | 2015053739 A1 | 4/2015 |

OTHER PUBLICATIONS

Angelo, "Micronutrients and Bone Health", Linus Pauling Institute, [accessed on Oct. 20, 2015, retrieved from the Internet: <http://lpi.oregonstate.edu/infocenter/bonehealth.html>].

Anghileri, et al., "Neuronal Differentiation Potential of Human Adipose-Derived Mesenchymal Stem Cells", Stem Cells Dev., vol. 17, No. 5, pp. 909-916, (2008).

Arnalich-Montiel, et al., "Adipose-Derived Stem Cells Are a Source for Cell Therapy of the Corneal Stroma", Stem Cells, vol. 26, pp. 570-579, (2008).

Aubin, et al., Isolation of Bone Cell Clones with Differences in Growth, Hormone Responses, and Extracellular Matrix Production, 92 J. Cell. Biol. 452-61, (1982).

Baer, et al., "Adipose-Derived Mesenchymal Stromal/Stem Cells: Tissue Localization, Characterization, and Heterogeneity," Stem Cells International, Hidsawi Publishing, vol. 2012, Article ID 812693, 11 pages.

Barry, "Mesenchymal stem cell therapy in joint disease," Tissue engineering of cartilage and bone: Novartis Foundation Symposium, 249, 86-102 (2003).

Bennett, et al., Adipocytic cells cultured from marrow have osteogenic potential, 99 J. Cell. Sci. 131 (1991).

Boquest, A., et al., "Isolation of Stromal Stem Cells From Human Adipose Tissue,", Nuclear Reprogramming: Methods and Protocols, vol. 325, Chapter 4, 35-46 Humana Press, New Jersey, (2006).

Bruder, et al., "Tissue Engineering of Bone. Cell Based Strategies", Clin Orthop Relat Res., vol. 367 Suppl., pp. S68-S83, (1999).

Bunnell, et al., "Adipose-Derived Stem Cells: Isolation, Expansion and Differentiation", Methods, vol. 45, No. 2, pp. 115-120, (2008).

Butt, et al., "Stimulation of Peri-Implant Vascularization with Bone Marrow-Derived Progenitor Cells: Monitoring by in Vivo EPR Oximetry", Tissue Eng., vol. 13, No. 8, pp. 2053-2061, (2007).

Cha, et al., "Stem cells in cutaneous wound healing," Clinics in Dermatology 25:73-78 (2007).

Chamberlain, et al., "Concise Review: Mesenchymal Stem Cells: Their Phenotype, Differentiation Capacity, Immunological Features, and Potential for Homing," Stem Cells, 25:2739-2749, (2007).

Chen, et al., "Differentiation of Rat Adipose-Derived Stem Cells into Smooth-Muscle-Like Cells in Vitro", Zhonghua Nan Ke Xue, 2009, vol. 15, No. 5, pp. 425-430, (2009).

Chen, et al., "Study of MSCs in Vitro Cultured on Demineralized Bone Matrix of Mongrel", Shanghai Kou Qiang Yi Xue, vol. 16, No. 3, pp. 255-258, (2007).

Cheng, et al., "Chondrogenic Differentiation of Adipose-Derived Adult Stem Cells by a Porous Scaffold Derived from Native Articular Cartilage Extracellular Matrix", Tissue Eng Part A, vol. 15, No. 2, pp. 231-241, (2009).

Chu, et al. "Leukocytes in blood transfusion: adverse effects and their prevention," HKMJ, 5:280-284, (1999).

Chung, et al., "Bladder Reconstitution with Bone Marrow Derived Stem Cells Seeded on Small Intestinal Submucosa Improves Morphological and Molecular Composition," J. Urology 174:353-359 (2005).

Crapo, P. et al., "An overview of tissue and whole organ decellulaiizalion processes," Biomaterials 32(12):3233-3243 (2011).

Cui, et al., "Repair of Cranial Bone Defects with Adipose Derived Stem Cells and Coral Scaffold in a Canine Model", Biomaterials, vol. 28, pp. 5477-5486, (2007).

Damien, et al., "Bone Graft and Bone Graft Substitutes: A Review of Current Technology and Applications", Journal Applied Biomaterials, vol. 2, pp. 187-208, (1991).

Dastoor et al., "Adermal Fillers for Facial Soft Tissue Augmentation." Journal of Oral Implantology, vol. XXXIII, No. Four, pp. 191-204, (2007).

Davis, et al. "Review: Regulation of Tissue Injury Reponses by the Exposure of Matricryptic Sites within Extracellular Matrix Molecules," American Journal of Pathology, vol. 156, No. 5, 10 pages, May 2005.

De Girolamo, et al. "Osteogenic Differentiation of Human Adipose-Derived Stem Cells: Comparison of Two Different Inductive Media", J Tissue Eng Regen Med, 2007, vol. 1, No. 2, pp. 154-157, (2007).

De Girolamo, et al., "Human Adipose-Derived Stem Cells as Future Tools in Tissue Regeneration: Osteogenic Differentiation and Cell-Scaffold Interaction", Int J Artif Organs, vol. 31, No. 6, pp. 467-479, (2008).

De Long, et al., "Bone Grafts and Bone Graft Substitutes in Orthpaedic Trauma Surgery. A Critical Analysis", The Journal of Bone & Joint Surgery, vol. 89, pp. 649-658, (2007).

De Ugarte, et al., "Comparison of Multi-Lineage Cells from Human Adipose Tissue and Bone Marrow", Cells Tissues Organs, vol. 174, No. 3, pp. 101-109, (2003).

Diekman, et al., "Chondrogenesis of adult stem cells from adipose tissue and bone marrow: Induction by growth factors and cartilage-derived matrix," Tissue Engineering, 16, 523-533, (2010); pub. online Sep. 2009.

Di Bella, et al., "Bone Regeneration in a Rabbit Critical-Sized Skull Defect Using Autologous Adipose-Derived Cells", Tissue Eng Part A., vol. 14, No. 4, pp. 483-490, (2008).

Dubois, et al.; "Chapter 5: Isolation of Human Adipose-derived Stem Cells from Biopsies and Liposuction Specimens"; Methods in Molecular Biology, vol. 449, 2008, pp. 69-79, (2008).

Elabd, et al., "Human Adipose Tissue-Derived Multipotent Stem Cells Differentiate in Vitro and in Vivo into Osteocyte-Like Cells", Biochem Biophys Res Commun., vol. 361, No. 2, pp. 342-348, (2007).

Extended European Search Report for EP Patent Application No. 13895259.3, dated Aug. 29, 2016, all pages.

Extended European Search Report for EP Patent Application No. 14771001.6, dated Sep. 23, 2016, all pages.

Extended European Search Report for European Patent Application No. 16183850.3, dated Sep. 27, 2016, all pages.

Eyre, "Collagen of articular cartilage", D. Collagen of Articular Cartilage, Arthritis Res. vol. 4 No. 1, pp. 30-35, Oct. 5, 2001.

Filipak, Michiko et al., "Tumor Necrosis Factor Inhibits the Terminal Event in Mesenchymal Stem Cell Differentiation", 137, J. Cell. Phys. 368, 367-73 (1988).

Finkemeier, "Bone Grafting and Bone-Graft Substitutes"; The Journal of Cone and Joint Surgery, pp. 454-464; vol. 84-A, No. 3, Mar. 2002.

"Flowable" Definition: Merriam-Webster, retrieved from the internet Apr. 2, 2018:<http://www.merriam-webster.com/dictionary/flowable>, 6 pages.

(56) References Cited

OTHER PUBLICATIONS

"Flowing" Definition: Merriam-Webster, retrived from the internet Apr. 2, 2018:<http://www.merriam-webster.com/dictionary/flowing>, 6 pages.

Flynn, L., et al., "Adipose Tissue Engineering With Naturally Derived Scaffolds and Adipose-Derived Stem Cells", Biomaterials, vol. 28, No. 26, pp. 3834-3842, (2007).

Flynn, L., et al., "Proliferation and Differentiation of Adipose-Derived Stem Cells on Naturally Derived Scaffolds", Biomaterials, vol. 29, No. 12, pp. 1862-1871, (2008).

Fraser, JK, et al., "Adipose-Derived Stem Cells", Methods Mol Bio., vol. 449, pp. 59-67, (2008).

Freed, L.E. et al., Joint resurfacing using allograft chondrocytes and synthetic biodegradable polymer scaffolds, 28 J. Biomed. Mater. Res. 891 (1994).

Gamradt, et al., "Bone Graft for Revision Hip Arthroplasty: Biology and Future Applications", Clin Orthop Relat D Res., vol. 417, pp. 183-194, (2003).

Gepstein, et al. "Bridging Large Defects in Bone by Demineralized Bone Matrix in the Form of a Powder"; The Journal of Bone and Joint Surgery, pp. 984-992; vol. 69-A, No. 7, Sep. 1987.

Ghanavi, et al. "The rationale for using microscopic units of a donor matrix in cartilage defect repair", Cell Tissue Res., 347: pp. 643-648, (2012).

Gilbert et al., "Quantification of DNA in Biologic Scaffold Materials," J. Surg Res 152:135-139 (2009).

Gimble, et al., "Differentiation Potential of Adipose Derived Adult Stem (ADAS) Cells", Curr top Dev Bioi., vol. 58, pp. 137-160, (2003).

Gimble, J., et al., "Adipose-Derived Adult Stem Cells: Isolation, Characterization, and Differentiation Potential", Cytotherapy, vol. 5, No. 5, pp. 362-369, (2003).

Glowacki, et al., "Application of the Biological Principle of Induced Osteogenesis for Craniofacial Defects", The Lancet, pp. 959-962, (1981).

Goh, et al., "Cryopreservation Characteristics of Adipose Derived Stem Cells: Maintenance of 6 Differentiation Potential and Viability", Journal of Tissue Engineering and Regenerative Medicine, vol. 1, pp. 322-324, (2007).

Gomes, et al., "Tissue Engineering: Key Elements and Some Trends", Macromolecular Bioscience, vol. 4, pp. 737-742, (2004).

Greenwald, et al., "Bone-Graft Substitutes: Facts, Fictions, and Applications", The Journal of Bone & Joint Surgery, vol. 83, pp. 98-103, (2001).

Grewal, et al., "BMP-2 Does Not Influence the Osteogenic Fate of Human Adipose-Derived Stem Cells", Plast Reconstr Surg., vol. 123 (2 Suppl), pp. 158S-165S, (2009).

Grigoriadis, A.E. et al., Differentiation of Muscle, Fat, Cartilage, and Bone from Progenitor Cells Present in a Bone-derived Clonal Cell Population: Effect of Dexamethasone, 106, J. Cell. Biol. 2144, 2139-51 (1988).

Halfon et al., "Markers Distinguishing Mesenchymal Stem Cells from Fibroblasts Are Downregulated with Passaging," Stem Cells Dev. 20:53-66 (2011).

Hanson et al., "Mesenchymal Stem Cell Therapy for Non-healing Cutaneous Wounds," Plast. Reconstr. Surg. 125:510-6 (2010).

Hayashi, et al., "Comparison of Osteogenic Ability of Rat Mesenchymal Stem Cells from Bone Marrow, Periosteum, and Adipose Tissue", Calcif Tissue Int., vol. 82, No. 3, pp. 238-247, (2008).

Hicok et al., Human adipose-derived adult stem cells produce osteoid in vivo, Tissue Engineering, vol. 10, No. 3/4, pp. 371-382, (2004).

Honsawek, S., et al., Effects of Demineralized Bone Matrix on Proliferation and Osteogenic Differentiation of Mesenchymal Stem Cells from Human Umbilical Cord, J Med Assoc Thai, vol. 89, Suppl 3, pp. 189-195, (2006).

Huang et al., "Adipose-Derived Stem Cells Seeded on Acellular Dermal Matrix Grafts Enhance Wound Healing in a Murine Model of a Full-Thickness Defect," Annals of Plastic Surgery, vol. 69, No. 6, pp. 656-662, Dec. 2012.

Hutmacher, et al., "State of the Art and Future Directions of Scaffold-Based Bone Engineering from a Biomaterials Perspective", Journal of Tissue Engineering and Regenerative Medicine, vol. 1, pp. 245-260, (2007).

International Preliminary Report on Patentability for International Application No. PCT/US2013/063674 filed Oct. 7, 2013, dated Apr. 21, 2016, 10 pages.

International Search Report and Written Opinion dated Jun. 29, 2010 for International Application No. PCT/US2009/064611, 7 pages.

International Search Report and Written Opinion of International Application No. PCT/US14/24223, dated Jun. 18, 2014, 17 pages.

International Search Report issued in connection with corresponding International Application No. PCT/US13/63674, dated Jan. 29, 2014, 7 pages.

Jeon, et al., "In Vivo Bone Formation Following Transplantation of Human Adipose-Derived Stromal Cells That Are Not Differentiated Osteogenically", Tissue Engineering Part A, vol. 14. No. 8., pp. 1285-1294, Aug. 2008.

Jin, et al., "Tissue Engineered Cartilage from hTGF beta2 Transduced Human Adipose Derived Stem Cells Seeded in PLGA/Aiginate Compound in Vitro and in Vivo", J Biomed Mater Res A, vol. 86, No. 4, pp. 1077-1087, (2008).

Juncosa-Melvin, et al., "Effects of Cell-to-Collagen Ratio in Stem Cell-Seeded Constructs for Achilles Tendon Repair", Tissue Engineering, vol. 12 No. 4, pp. 681-689, (2006).

Jurgens, Wouter J.F. et al., "Effect of tissue-harvesting site on yield of stem cells derived from adipose tissue: implications for cell-based therapies," Cell Tissue Res, 332:415-426, (2008).

Kakudo, et al., "Bone Tissue Engineering Using Human Adipose-Derived Stem Cells and Honeycomb Collagen Scaffold", J Biomed Mater Res A, vol. 84, No. 1, pp. 191-197, (2008).

Kasten, P., et al., "Ectopic Bone Formation Associated With Mesenchymal Stem Cells in a Resorbable Calcium D Deficient Hydroxyapatite Carrier", Biomaterials, vol. 26, No. 29, pp. 5879-5889, (2005).

Kasten, P., et al., "Induction of Bone Tissue on Different Matrices: An In Vitro and a In Vivo Pilot Study in the SCID Mouse", Z Orthop Ihre Grenzgeb., vol. 142, No. 4, pp. 467-475, (2004).

Kim, et al., "Chondrogenic Differentiation of Adipose Tissue-Derived Mesenchymal Stem Cells: Greater Doses of Growth Factor are Necessary", J Orthop Res, vol. 27, No. 5, pp. 612-619, (2009).

Kim, Y.J., et al., "Direct Comparison of Human Mesenchymal Stem Cells Derived from Adipose Tissues and Bone Marrow in Mediating Neovascularization in Response to Vascular Ischemia." Cell Physiol Biochem, 20(6): 867-876 (2007).

Kingham, et al., "Adipose-Derived Stem Cells Differentiate into a Schwann Cell Phenotype and Promote Neurite Outgrowth in Vitro", Exp Neurol., vol. 207, No. 2, pp. 267-274, (2007).

Ko, et al., "In Vitro Osteogenic Differentiation of Human Mesenchymal Stem Cells and In Vivo Bone Formation in Composite Nanofiber Meshes", Tissue Eng Part A., vol. 14, No. 12, pp. 2105-2119, (2008).

Kobienia, M.D., "Alloderm in Breast Reconstruction", Kobienia Plastic Surgery, Jul. 1, 2011. Retrieved from the internet: <https://www.drkobienia.com/blog/2011/06/30/alloderm-in-breast-reconstruction-54686>.

Kroeze, RJ; "Adipose stem cells on a biodegradable polymer for spinal fusion" Vrije Universiteit, 178 pages, Dec. 19, 2014.

Langer, et al., "Tissue Engineering", Science, vol. 260, No. 5110, pp. 920-926, May 14, 1993.

Le Blanc, K., et al., "HLA Expression and Immunologic Properties of Differentiated and Undifferentiated Mesenchymal Stem Cells", Experimented Hematology, pp. 890-896, (2003).

Lecoeur, L.et al., "In vitro induction of osteogenic differentiation from non-osteogenic mesenchymal cells", Biomaterials 18, 989-993, Jan. 11, 1997.

Li, et al., "Bone Regeneration by Implantation of Adipose-Derived Stromal Cells Expressing BMP-2", Biochem Ciophys Res Commun, vol. 356, No. 4, pp. 836-842, (2007).

Lifecell, "Alloderm Select™ Regenerative Tissue Matrix" Product Brochure. (2018), retrieved from the internet: <http://www.lifecell.com/products/allodermtm/selecttm-regenerative-tissue-matrix/>.

(56) References Cited

OTHER PUBLICATIONS

Lin et al., "Commonly used mesenchymal stem cell markers and tracking labels: Limitations and challenges," Histol. Histopathol. 28:1109-1116 (2013).
Lin, et al., "Comparison of Osteogenic Potentials of BMP4 Transduced Stem Cells from Autologous Bone Marrow and Fat Tissue in a Rabbit Model of Calvarial Defects", Calcif Tissue Int., vol. 85, No. 1, pp. 55-56, (2009).
Liu, et al., "Evaluation of Partially Demineralized Osteoporotic Cancellous Bone Matrix Combined with 4 Human Bone Marrow Stromal Cells for Tissue Engineering: An In Vitro and In Vivo Study", Calcif Tissue Int., vol. 83, No. 3, pp. 176-185, (2008).
Liu, et al., "Evaluation of the Viability and Osteogenic Differentiation of Cryopreserved Human Adipose-Derived Stem Cells", Cryobiology, vol. 57, pp. 18-24, (2008).
Liu, G., et al., "Tissue-Engineered Bone Formation with Cryopreserved Human Bone Marrow Mesenchymal Stem D Cells", Cryobiology, 2008, vol. 56, No. 3, pp. 209-215.
Liu, G., et al., "Evaluation of Partially Demineralized Osteoporotic Cancellous Bone Matrix Combined with Human Bone Marrow Stromal Cells for Tissue Engineering: An In Vitro and In Vivo Study." Calcif. Tissue Int. 83(3): 176-185 (Sep. 2008).
Lovric et al., "The Effect of Processing Conditions of the Osteoinductivity of Sheep Demineralized Bone Matrix in an Ectopic Nude Rat Model: A Pilot Study", ORS 2012 Annual Meeting, Poster No. 0629.
Masuno, H. et al., Synthesis of inactive nonsecretable high mannose-type lipoprotein lipase by cultured brown adipocytes of combined lipase-deficient cld/cld mice, 265 J. Biol. Chem. 1628 (1990).
Mauney, et al., "In Vitro and in Vivo Evaluation of Differentially Demineralized Cancellous Bone Scaffolds Combined with Human Bone Marrow Stromal Cells for Tissue Engineering", Biomaterials, vol. 26, pp. 3173-3185, (2005).
Mauney. et al., "Osteogenic Differentiation of Human Bone Marrow Stromal Cells on Partially Demineralized Bone Scaffolds in Vitro", Tissue Engineering, vol. 10. No. 1-2, pp. 81-92, Jan. 2004.
Medtronic Product Brochure: "INFUSE Bone Graft", retrieved from the internet Mar. 5, 2017: (www.infusebonegraft.com/healthcare-providers/bone-grafting-options/categorization-of-bone-grafts/allograft-tissue/index.htm).
Mehlhorn, et al., "Chondrogenesis of Adipose-Derived Adult Stem Cells in a Poly-Lactide-Co-Giycolide Scaffold", 0 Tissue Eng Part A, vol. 15, No. 5, pp. 1159-1167, (2009).
Merceron, et al., "Adipose-Derived Mesenchymal Stem Cells and Biomaterials for Cartilage Tissue Engineering", Joint Bone Spine, vol. 75, No. 6, pp. 672-674, (2008).
Minana, Maria-Dolores et al., "IFATS Collection: Identification of Hemangioblasts in the Adult Human Adipose Tissue," Stem Cells, 26:2696-2704, (2008).
Mischen, et al., "Metabolic and Functional Characterization of Human Adipose-Derived Stem Cells in Tissue Engineering", Plast Reconstr Surg., vol. 22, No. 3, pp. 725-738, (2008).
Mitchell, J.B., e al. "Immunopheynotype of Human Adipose-Derived Cells: Temporal Changes in Stromal-Associated and Stem Cell-Associated Markers", Stem Cells, vol. 24, pp. 376-385, (2006).
Mizuno, "Adipose-Derived Stem Cells for Tissue Repair and Regeneration: Ten Years of Research and a Literature Review", J Nippon Med Sch., vol. 76, No. 2, pp. 56-66, (2009).
Mulliken, et al., "Induced Osteogenesis—The Biological Principle and Clinical Applications", Journal of Surgical Research, vol. 37, pp. 487-496, (1984).
Mulliken, et al., "Use of Demineralized Allogeneic Bone Implants for the Correction of Maxillocraniofacial Deformities", Ann Surg., vol. 194, No. 3, pp. 366-372, (1981).
Niemeyer, et al., "Comparison of Immunological Properties of Bone Marrow Stromal Cells and Adipose Tissue-Derived Stem Cells Before and After Osteogenic Differentiation in Vitro", Tissue Eng., vol. 13, No. 1, pp. 111-121, (2007).
Nih et al., "Stem Cell Basics", National Institute of Health, [accessed on Oct. 20, 2015, retrieved from the Internet: <http://stemcells.nih.gov/info/basics/pages/basics4.aspx>].
Noel, et al., "Cell Specific Differences Between Human Adipose-Derived and Mesenchymal-Stromal Cells Despite Similar Differentiation Potentials", Exp Cell Res., vol. 314, No. 7, pp. 1575-1584, (2008).
Notice of Allowance dated Sep. 25, 2015 for U.S. Appl. No. 14/200,353, filed Nov. 4, 2009, all pages.
Office Action dated Apr. 10, 2013 in U.S. Appl. No. 12/965,335, 23 pages.
Office Action dated Jan. 15, 2015 in U.S. Appl. No. 12/612,583, 26 pages.
Office Action dated May 7, 2013 for U.S. Appl. No. 12/612,583, filed Nov. 4, 2009 First Names Inventor: Yaling Shi; 41 pages.
Office Action dated Sep. 9, 2013 for U.S. Appl. No. 12/612,583, filed Nov. 4, 2009; First Names Inventor: Yaling Shi; 26 pages.
Pate, D.W. et al., "Isolation and differentiation of mesenchymal stem cells from rabbit muscle", Proceedings for the 49$^{th}$ annual sessions of the forum on fundamental surgical Problems, vol. XLIV, pp. 586-589, Oct. 10-15, 1993.
Pietrzak, et al., "Assay of Bone Morphogenetic Protein-2, -4, and -7 in Human Demineralized Bone Matrix", Scientific Foundation, The Journal of Craniofacial Surgery, vol. 17, No. 1; pp. 84-90, Jan. 2006.
Prockop, OJ, et al., "Isolation and Characterization of Rapidly Self-Renewing Stem Cells from Cultures of Human Marrow Stromal Cells", Cytotherapy, vol. 3, No. 5, pp. 393-396, (2001).
Qian, et al., "Reconstruction of Bone Using Tissue Engineering and Nanoscale Technology", Zhongguo Xiu Fu Chong Jian Wai Ke Za Zhi, vol. 20, No. 5, pp. 560-564, (2006).
Rada, et al., "Adipose Tissue-Derived Stem Cells and Their Application in Bone and Cartilage Tissue Engineering", Tissue Engineering: Part B, vol. 15, No. 2, pp. 113-125, (2009).
Reddi, "Morphogenesis and Tissue Engineering of Bone and Cartilage: Inductive Signals, Stem Cells, and Biomimetic Biomaterials", Tissue Eng., vol. 6, No. 4, pp. 351-359, (2000).
Reddi, "Role of Morphogenetic Proteins in Skeletal Tissue Engineering and Regeneration", Nat Biotechnol., vol. 16, No. 3, pp. 247-252, (1998).
Reddi, et al., "Biochemical Sequences in the Transformation of Normal Fibroblasts in Adolescent Rats", Proc. Nat. Acad. Sci. USA vol. 69, No. 6, pp. 1601-1605, Jun. 1972.
Rhie, Jong-Won et al., "Chondrogenic differentiation of human adipose-derived stem cells in PLGA (Poly(Lactide-co-Glycolide Acid)) Scaffold," Key Engineering Materials, 342, 345-348 (2007).
Rickard, D.J., Induction of rapid osteoblast differentiation in rat bone marrow stromal cell cultures by dexamethasone and BMP-2, 161 Dev. Biol. 218 (1994).
Rigotti, et al., "Clinical Treatment of Radiotherapy Tissue Damage by Lipoaspirate Transplant: A Healing Process Mediated by Adipose-Derived Adult Stem Cells", Plast Reconstr Surg., vol. 119, No. 5, pp. 1409-1422, (2007).
Riordan, NH et al., "Non-expanded adipose stromal vascular fraction cell therapy for multiple sclerosis," Journal of Translational Medicine , 7:29, 9 pages, (2009).
Sakaguchi et al., Comparison of human stem cells derived from various mesenchymal tissues, Arthritis & Rheumatism, vol. 52, No. 8, pp. 2521-2529, Aug. 2005.
Salgado, Antonio J. et al., Adult Stem Cells in Bone and Cartilage Tissue Engineering:, Current Stem Cell Research & Therapy, 1: pp. 345-364, (2006).
Schwartz, et al. "Osteoinductivity of Demineralized Bone Matrix is Independent of Donor Bisphosphonate Use"; The Journal of Bone and Joint Surgery; vol. 93-A, No. 24; pp. 2278-2286; Dec. 21, 2011.
Sclafani, Anthony, "Micronized Acellular Tissue for Soft Tissue Augmentation" A.P. Aesthetic Surgery Journal, 341-342, 20(4), (2000).
Sgaglione, "The Future of Cartilage Restoration." The Journal of Knee Surgery, vol. 17, No. 4., pp. 235-243, Oct. 2004.
Shi, et al., "Adipose-Derived Stem Cells Combined with a Demineralized Cancellous Bone Substrate for Bone Regeneration" Tissue Engineering Part A, vol. 8, pp. 1313-1321, Jun. 2012.

(56) References Cited

OTHER PUBLICATIONS

Shih, et al., "Restoration of bone defect and enhancement of bone ingrowth using partially demineralized bone matrix and marrow stromal cells", Journal of Orthopaedic Research, vol. 23., No. 6, pp. 1293-1299, Nov. 2005.
Simper, et al., "Smooth Muscle Progenitor Cells in Human Blood", Circulation (by the American Heart Association), vol. 106, pp. 1199-1204, Aug. 19, 2002.
Singh, Shikha et al., "Leukocyte depletion for safe blood transfusion," Biotechnol J., 4:1140-1151, (2009).
Strem, et al., "Multi-potential Differentiation of Adipose Tissue-Derived Stem Cells", Keio J Med., vol. 54, No. 3, pp. 132-141, (2005).
Strong, et al. "Freeze-Drying of Tissues," Musculoskeletal Tissue Banking, (WW Tomford ed.) Ravens Press, NY, 28 pages, (1993).
"Substrate",(n.d.). The American Heritage® Stedman's Medical Dictionary, [accessed on Oct. 20, 2015, retrieved from the Internet: <http://dictionary.reference.com/browse/substrate>].
Tan et al., "Meniscus Reconstruction Through Co-culturing Meniscus Cells with Synovium-Derived Stem Cells on Small Intestine Submucosa—A Pilot Study to Engineer Meniscus Tissue Constructs," Tissue Eng. Part A 16:67-79 (2010).
Tapp, et al., "Adipose-Derived Stem Cells: Characterization and Current Application in Orthpaedic Tissue Repair", Exp Bioi Med (Maywood), vol. 234, No. 1, pp. 1-9, (2009).
Truong et al., "Comparison of Dermal Substitutes in Wound Healing Utilizing a Nude Mouse Model," Journal of Burns and Wounds, vol. 4, pp. 72-82, published online Mar. 14, 2005.
Tsiridis, et al., "In Vitro and In Vivo Optimization of Impaction Allografting by Demineralization and Addition of rh-OP-1", J Orthop Res, vol. 25, No. 11, pp. 1425-1437, (2007).
U.S. Appl. No. 61/115,457, filed Nov. 17, 2008.
Unknown "Preparation of the stromal vascular fraction (SVF) from human lipaspirate" Miltenyi Biotec, (2008).
Urist, M., "Bone Formation by Autoinduction", *Science*, vol. 150, No. 3698, pp. 893-899. Nov. 12, 1965.
Van Dijk, et al., "Differentiation of Human Adipose-Derived Stem Cells Towards Cardiomyocytes as Facilitated by Laminin", Cell Tissue Res, vol. 334, No. 3, pp. 457-467, (2008).
Van, R.L. et al., Cytological and enzymological characterization of adult human adipocyte precursors in culture, 58 J. Clin. Invest. 699 (1976).
Varma, MJO et al., "Phenotypical and Functional Characterization of Freshly Isolated Adipose Tissue-Derived Stem Cells," Stem Cells and Development, 16:91-104 (2007).
Venkatasubramanian, et al. "Effects of Freezing and Cryopreservation on the Mechanical Properties of Arteries," Annals of Biomedical Engineering, vol. 34, No. 5, 10 pages, May 2006.

Wang, et al., "Characterization of Demineralized Bone Matrix-Induced Osteogenesis in Rat Calvarial Bone Defects: III. Gene and Protein Expression", Calcif Tissue Int., vol. 67, No. 4, pp. 314-320, (2000).
Wang, J., et al., "Characterization of Matrix-Induced Osteogenesis in Rat Calvarial Bone Defects: I. Differences in the Cellular Response to Demineralized Bone Matrix Implanted in Calvarial Defects and in Subcutaneous Sites", Calcif Tissue Int., vol. 65, No. 2, pp. 156-165, (1999).
Wang, J., et al., "Characterization of Matrix-Induced Osteogenesis in Rat Calvarial Bone Defects: II. Origins of Bone-Forming Cells", CalcifTissue Int., vol. 65, No. 6, pp. 486-493, (1999).
Wei, et al., "A Novel Injectable Scaffold for Cartilage Tissue Engineering Using Adipose-Derived Adult Stem Cells", J Orthop Res., vol. 26, No. 1, pp. 27-33, (2008).
Wei, et al., "Adipose-Derived Stem Cells and Chondrogenesis", Cytotherapy, vol. 9, No. 8, pp. 712-716, (2007).
Xie, et al., "The Performance of a Bone-Derived Scaffold Material in the Repair of Critical Bone Defects in a D Rhesus Monkey Model", Biomaterials, vol. 28, No. 22, pp. 3314-3324, (2007).
Yang, Qiang et al., "A cartilage ECM-derived 3-D porous acellular matrix scaffold for in vivo cartilage tissue engineering with PKH26-labeled chondrogenic bone marrow-derived mesenchymal stem cells," Biomaterials, 29, 2378-2387 (2008).
Yin et al., "Stem cells for tendon tissue engineering and regeneration," Expert Opin. Biol. Ther. 10:689-700 (2010).
Yin, et al. "Vitreous cryopreservation of tissue engineered bone composed of bone marrow mesenchymal stem cells and partially demineralized bone matrix", Cryobiology, vol. 59, pp. 180-187, (2009).
Yoo et al., "Tissue Engineering of Injectable Soft tissue Filler: Using Adipose Stem Cells and Micronized Acellular Dermal Matrix." J. Korean Med Sci. vol. 24, pp. 104-109, (2009).
Yoo, et al., "Comparison of Immunomodulatory Properties of Mesenchymal Stem Cells Derived from Adult Human Tissues", Cell Immunol., vol. 259, No. 2, pp. 150-156, (2009).
Yoon, et al., "In Vivo Osteogenic Potential of Human Adipose-Derived Stem Cells/Poly Lactide-Co-Glycolic Acid Constructs for Bone Regeneration in a Rat Critical-Sized Calvarial Defect Model", Tissue Eng., vol. 13, No. 3, pp. 619-627, (2007).
Yoshimura, et al., "Comparison of Rat Mesenchymal Stem Cells Derived from Bone Marrow, Synovium, Periosteum, Adipose Tissue, and Muscle", Cell Tissue Res., vol. 327, No. 3, pp. 449-462, (2007).
Young, H.E. et al., Pluripotent mesenchymal Stem Cells Reside within Avian Connective Tissue Matrices, In Vitro Cell. Div. Biol. 29A, pp. 723-736, Sep. 1993.
Zhang, et al., "Adipose Tissue Engineering with Human Adipose-Derived Stem Cells and Fibrin Glue Injectable Scaffold", Zhonghua Yi Zue Za Zhi, vol. 88, No. 38, pp. 2705-2709, (2008).
Zhao, L. et al., "The study of the feasibility of segmental bone defect repair with tissue-engineered bone membrane: a qualitative observation," Strat. Traum. Limb Recon. 3:57-64 (2008).

* cited by examiner

CELL REPOPULATED COLLAGEN MATRIX FOR SOFT TISSUE REPAIR AND REGENERATION

CROSS-REFERENCE TO RELATED APPLICATIONS

This application is a continuation of U.S. patent application Ser. No. 14/938,173, filed Nov. 11, 2015, which is a continuation of U.S. patent application Ser. No. 14/207,220, filed Mar. 12, 2014, now abandoned, which claims the benefit of priority of U.S. Provisional Application No. 61/790,412, filed Mar. 15, 2013, the contents of each of which are incorporated herein by reference in their entireties.

BACKGROUND OF THE INVENTION

Injuries to soft tissues, such as skin, muscle, connective tissue, or vascular tissue, are common occurrences. In some instances, minor soft tissue injuries are able to self-repair without any outside intervention, but frequently the extent of an injury is severe enough, or the capacity of the soft tissue to self-repair is limited enough, that surgical intervention is required. Surgery to repair a soft tissue injury generally entails implanting or applying a biocompatible material that is meant to replace the missing or defective tissue (for example, using a graft to replace a torn tendon or ligament). However, even with surgical intervention, the process of repairing or reconstructing the injured soft tissue can be slow or incomplete.

Stem cells have been shown to be useful in promoting wound healing and the repair of injuries to soft tissues such as tendons and ligaments. See, e.g., Yin et al., *Expert Opin. Biol. Ther.* 10:689-700 (2010); Hanson et al., *Plast. Reconstr. Surg.* 125:510-6 (2010); and Cha and Falanga, *Clin. Dermatol.* 25:73-8 (2007). Stem cells have also been used to promote soft tissue reconstruction, for example using stem cell-seeded small intestinal submucosa to promote bladder reconstitution and meniscus reconstruction. Chung et al., *J. Urol.* 174:353-9 (2005); Tan et al., *Tissue Eng. Part A* 16:67-79 (2010).

BRIEF SUMMARY OF THE INVENTION

In one aspect, the present invention provides compositions for treating a soft tissue injury in a subject. In some embodiments, the composition comprises a collagen matrix and mesenchymal stem cells adhered to the collagen matrix, wherein the mesenchymal stem cells are derived from a tissue processed to form a cell suspension comprising mesenchymal stem cells and non-mesenchymal stem cells that is seeded onto the collagen matrix, and wherein the mesenchymal stem cells are not cultured ex vivo after formation of the cell suspension and prior to seeding of the cell suspension on the collagen matrix.

In some embodiments, the collagen matrix is skin, dermis, tendon, ligament, muscle, amnion, meniscus, small intestine submucosa, or bladder. In some embodiments, the collagen matrix is decellularized dermis. In some embodiments, the collagen matrix is dermis from which the epidermis layer has been removed.

In some embodiments, the collagen matrix is treated to reduce immunogenicity. In some embodiments, the treated collagen matrix has at least 50% fewer endogenous cells than a corresponding untreated collaged matrix of the same type. In some embodiments, the treated collagen matrix has a DNA content that is decreased by at least 50% as compared to a corresponding untreated collaged matrix of the same type. In some embodiments, the treated collagen matrix is non-immunogenic.

In some embodiments, the treated collagen matrix retains bioactive cytokines. In some embodiments, the bioactive cytokines are selected from the group consisting of IL-4, IL-6, IL-15, IL-16, IL-18, and IL-28. In some embodiments, the treated collagen matrix retains bioactive growth factors. In some embodiments, the bioactive growth factor is platelet-derived growth factor alpha (PDGFa).

In some embodiments, the collagen matrix is human, porcine, bovine, or equine.

In some embodiments, the tissue that is processed to form the cell suspension is selected from adipose tissue, muscle tissue, birth tissue, skin tissue, bone tissue, or bone marrow tissue. In some embodiments, the tissue that is processed to form the cell suspension is human tissue.

In some embodiments, the collagen matrix and the tissue that is processed to form the cell suspension are from the same species. In some embodiments, the collagen matrix and the tissue that is processed to form the cell suspension are from different species. In some embodiments, the collagen matrix and the tissue that is processed to form the cell suspension are from the same donor. In some embodiments, the collagen matrix and the tissue that is processed to form the cell suspension are from different cadaveric donors. In some embodiments, the donor is human.

In some embodiments, mesenchymal stem cells seeded on the collagen matrix express one or more of the positive MSC markers CD105, CD144, CD44, CD166, or CD90. In some embodiments, mesenchymal stem cells seeded on the collagen matrix do not express one or more of the negative MSC markers CD34 and CD116.

In another aspect, the present invention provides methods of treating a soft tissue injury in a subject. In some embodiments, the method comprises contacting a composition as described herein (e.g., a composition comprising a collagen matrix and mesenchymal stem cells adhered to the collagen matrix, wherein the mesenchymal stem cells are derived from a tissue processed to form a cell suspension comprising mesenchymal stem cells and non-mesenchymal stem cells that is seeded onto the collagen matrix, and wherein the mesenchymal stem cells are not cultured ex vivo after formation of the cell suspension and prior to seeding of the cell suspension on the collagen matrix) to the site of the soft tissue injury.

In some embodiments, the soft tissue injury is an injury to a tendon tissue, a ligament tissue, a meniscus tissue, a muscle tissue, a skin tissue, a bladder tissue, or a dermal tissue. In some embodiments, the soft tissue injury is a surgical wound, a trauma wound, a chronic wound, an acute wound, a deep channel wound, an exsanguinating site, or a burn.

In some embodiments, the composition is administered topically. In some embodiments, the composition is administered by surgical implantation.

In some embodiments, the subject is a human subject. In some embodiments, the subject is a veterinary subject. In some embodiments, the veterinary subject is a horse.

In yet another aspect, the present invention provides methods of making a composition for treating a soft tissue injury. In some embodiments, the method comprises:
  (a) digesting a tissue to form a cell suspension comprising mesenchymal stem cells and non-mesenchymal stem cells;
  (b) seeding the cell suspension onto a collagen matrix;

(c) incubating the collagen matrix seeded with the cell suspension under conditions suitable for adhering the mesenchymal stem cells to the collagen matrix; and (d) removing the non-adherent cells from the collagen matrix.

In some embodiments, prior to step (b), the method further comprises treating the collagen matrix to reduce immunogenicity. In some embodiments, treating the collagen matrix to reduce immunogenicity comprises contacting the collagen matrix with a decellularizing agent. In some embodiments, treating the collagen matrix to reduce immunogenicity comprises removing an epidermis layer without decellularizing the collagen matrix. In some embodiments, the treated collagen matrix has at least 50% fewer endogenous cells than a corresponding untreated collaged matrix of the same type. In some embodiments, the treated collagen matrix has a DNA content that is decreased by at least 50% as compared to a corresponding untreated collaged matrix of the same type. In some embodiments, the treated collagen matrix is non-immunogenic.

In some embodiments, the method further comprises a washing step to remove the decellularizing agent. In some embodiments, the washing step is performed after decellularization and before the cell suspension is seeded on the collagen matrix.

In some embodiments, the collagen matrix is skin, dermis, tendon, ligament, muscle, amnion, meniscus, small intestine submucosa, or bladder.

In some embodiments, the treated collagen matrix retains bioactive cytokines. In some embodiments, the bioactive cytokines are selected from the group consisting of IL-4, IL-6, IL-15, IL-16, IL-18, and IL-28. In some embodiments, the treated collagen matrix retains bioactive growth factors. In some embodiments, the bioactive growth factor is platelet-derived growth factor alpha (PDGFa).

In some embodiments, the collagen matrix is human, porcine, bovine, or equine.

In some embodiments, the tissue that is digested to form the cell suspension is selected from adipose tissue, muscle tissue, birth tissue, skin tissue, bone tissue, or bone marrow tissue. In some embodiments, the tissue that is digested to form the cell suspension is human tissue.

In some embodiments, the collagen matrix and the tissue that is digested to form the cell suspension are from the same species. In some embodiments, the collagen matrix and the tissue that is digested to form the cell suspension are from different species. In some embodiments, the collagen matrix and the tissue that is digested to form the cell suspension are from the same donor. In some embodiments, the collagen matrix and the tissue that is digested to form the cell suspension are from different cadaveric donors. In some embodiments, the donor is human.

Definitions

As used herein, the term "soft tissue" refers to a tissue that connects, supports, or surrounds organs and structures of the body, and which is not bone. Examples of soft tissues include, but are not limited to, tendon tissue, ligament tissue, meniscus tissue, muscle tissue, skin tissue, bladder tissue, and dermal tissue.

As used herein, the term "collagen matrix" refers to a biocompatible scaffold comprising collagenous fibers (e.g., collagen I) that provides a structural support for the growth and propagation of cells. In some embodiments, a collagen matrix is a biological tissue that has been harvested from a subject (e.g., a human or non-human animal). Examples of collagen sources include, but are not limited to, skin, dermis, tendon, ligament, muscle, amnion, meniscus, small intestine submucosa, or bladder. In some embodiments, the collagen matrix is from anatomical soft tissue sources (e.g., skin, dermis, tendon, or ligament) and not from bone or articular cartilage. In some embodiments, the collagen matrix primarily comprises type I collagen rather than type II collagen.

As used herein, the term "mesenchymal stem cell" refers to a multipotent stem cell (i.e., a cell that has the capacity to differentiate into a subset of cell types) that can differentiate into a variety of cell types, including osteoblasts, chondrocytes, and adipocytes. Mesenchymal stem cells can be obtained from a variety of tissues, including but not limited to bone marrow tissue, adipose tissue, muscle tissue, birth tissue (e.g., amnion, amniotic fluid, or umbilical cord tissue), skin tissue, bone tissue, and dental tissue.

The term "reduce immunogenicity" or "reduced immunogenicity" refers to a decreased potential to stimulate an immunogenic rejection in a subject. In some embodiments, a collagen matrix as described herein is treated to reduce its immunogenicity (i.e., decrease its potential to stimulate an immunogenic rejection in a subject in which the treated collagen matrix is implanted or topically applied) relative to a corresponding collagen matrix of the same type that has not been treated. The term "non-immunogenic," as used with reference to a collagen matrix, refers to a collagen matrix which does produce a detectable immunogenic response in a subject.

The terms "decellularized" and "acellular," as used with reference to a collagen matrix, refer to a collagen matrix from which substantially all endogenous cells have been removed from the matrix. In some embodiments, a decellularized or acellular collagen matrix is a matrix from which at least 70%, 75%, 80%, 85%, 90%, 91%, 92%, 93%, 94%, 95%, 96%, 97%, 98%, 99% or more of endogenous cells have been removed (e.g., by a decellularization treatment), relative to a corresponding collagen matrix of the same type which has not been subjected to removal of endogenous cells (e.g., has not been subjected to a decellularization treatment). Decellularization can be quantified according to any method known in the art, including but not limited to measuring reduction in the percentage of DNA content in a treated collagen matrix relative to an untreated collagen matrix or by histological staining. In some embodiments, a decellularized or acellular collagen matrix has a DNA content that is reduced by at least 50%, 60%, 70%, 80%, 90% or more as compared to an untreated collagen matrix.

The term "subject" refers to humans or other non-human animals including, e.g., other primates, rodents, canines, felines, equines, ovines, bovines, porcines, and the like.

The terms "treat," "treating," and "treatment" refer to delaying the onset of, retarding or reversing the progress of, or alleviating or preventing either the disease or condition to which the term applies, or one or more symptoms of such disease or condition.

BRIEF DESCRIPTION OF THE DRAWINGS

FIG. 4A shows Group C Top seeded cells, released. FIG. 4B shows unseeded control, no cells released from skin.

DETAILED DESCRIPTION OF THE INVENTION

I. Introduction

Figure 1A:
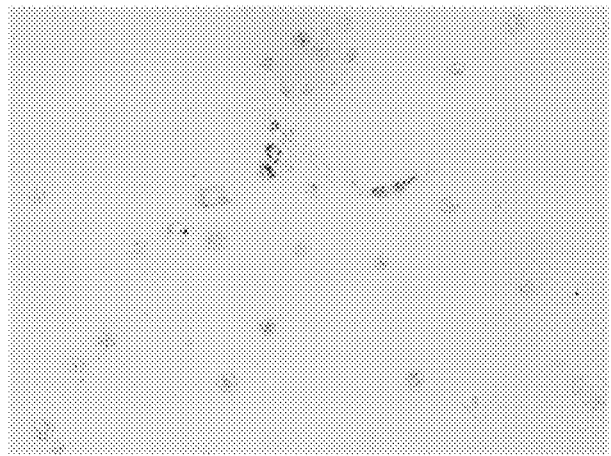
FIGS. 1A-1C show visual assessment of original (A), rinse (B), and final (C) wells as viewed under inverted microscope.

Collagen matrix-containing tissue products, such as small intestinal submucosa, can be applied to a soft tissue injury site to promote repair or reconstruction at the site of injury. It has previously been shown that seeding a collagen matrix-containing tissue product with stem cells promotes more rapid repair or reconstruction than occurs with a non-stem cell seeded collagen matrix tissue product. These results suggest that seeding stem cells on a collagen matrix may promote the rate and/or quality of soft tissue repair or regeneration.

However, previously described stem cell-seeded collagen matrices have utilized stem cells that are grown or proliferated ex vivo (e.g., on a plastic dish) prior to seeding the stem cells on the collagen matrix. Because cell populations change upon attachment to and proliferation on tissue culture plastic, culturing stem cells ex vivo prior to seeding the stem cells on a collagen matrix may result in undesirable phenotypic changes to the seeded stem cells.

Thus, in some embodiments the present invention provides compositions for treating soft tissue injuries comprising a collagen matrix and mesenchymal stem cells adhered to the collagen matrix, wherein the mesenchymal stem cells are derived from a tissue that has been processed (i.e., digested) to form a cell suspension comprising mesenchymal stem cells and non-mesenchymal stem cells that is seeded onto the collagen matrix, and wherein the mesenchymal stem cells are not cultured ex vivo (e.g., on a plastic dish) prior to seeding the cell suspension on the collagen matrix. The present invention also provides for methods of making said compositions comprising a collagen matrix and mesenchymal stem cells adhered to the collagen matrix and methods of treating a subject having a soft tissue injury using said compositions comprising a collagen matrix and mesenchymal stem cells adhered to the collagen matrix.

The present invention also relates to methods of preparing tissues for isolation of cell suspensions comprising mesenchymal stem cells. Cadaveric human tissue is regularly recovered from consented donors to be used in tissue product processing and medical device manufacturing. In some cases, cadaveric tissue may contain certain cell populations, such as progenitor cells or stem cells, which can be incorporated into therapeutic products and methods. Methods for obtaining progenitor cells or stem cells from such tissue have been described. For example, PCT Publication WO 2010/059565 to Shi, which is incorporated herein by reference, discloses techniques for isolating adipose derived stem cells from cadaver tissue.

In some embodiments, the present invention encompasses systems and methods for the pre-processing of various soft and fibrous tissues, prior to the isolation of progenitor and stem cell populations therefrom. For example, such preparatory techniques can be carried out on the cadaver tissue prior to isolation of the progenitor or stem cells, or prior to isolation of fractions containing such cells. In some cases, preparatory techniques can be performed on adipose tissue, prior to isolation of a stromal vascular fraction (SVF), a progenitor cell population, a stem cell population, or the like. Such isolated cell populations or fractions can be used in therapeutic treatments and products.

II. Compositions for Treating Soft Tissue Injuries

In one aspect, the present invention provides compositions for treating soft tissue injuries, wherein the composition comprises a collagen matrix and mesenchymal stem cells adhered to the collagen matrix. In some embodiments, the mesenchymal stem cells are derived from a tissue that has been processed (i.e., digested) to form a cell suspension comprising mesenchymal stem cells and non-mesenchymal stem cells that is seeded onto the collagen matrix and incubated under conditions suitable for adhering the mesenchymal stem cells to the collagen matrix.

In some embodiments, the mesenchymal stem cells are not cultured ex vivo after formation of the cell suspension and prior to seeding of the cell suspension on the collagen matrix. In some embodiments, the collagen matrix comprises more cells adhered to the outward (epidermal) side or surface of the collagen matrix than to the inward side or surface of the collagen matrix.

Collagen Matrix

A collagen matrix for use in the present invention can be from any collagenous tissue. In some embodiments, the collagen matrix is skin, dermis, tendon, ligament, muscle, amnion, meniscus, small intestine submucosa, or bladder. In some embodiments, the collagen matrix is not articular cartilage or bone. In some embodiments, the collagen matrix primarily comprises type I collagen rather than type II collagen.

In some embodiments, the collagen matrix is harvested from a subject, e.g., a human, bovine, ovine, porcine, or equine subject. In some embodiments, the collagen matrix is an engineered collagen matrix, e.g., a matrix that is engineered from one or more purified types of collagen, and optionally further comprising other components commonly found in collagen matrices, e.g., glycosaminoglycans. Engineered collagen matrix is known in the art and is readily commercially available.

In some embodiments, the collagen matrix that is seeded with a cell suspension is a flowable soft tissue matrix. For example, a collagen matrix can be prepared by obtaining a portion of soft tissue material, and cryofracturing the portion of soft tissue material, so as to provide a flowable soft tissue matrix composition upon thawing of the cryofractured tissue. Exemplary compositions and methods involving such flowable matrix materials are described in U.S. patent application Ser. No. 13/712,295, the contents of which are incorporated herein by reference.

In some embodiments, the collagen matrix is allogeneic to the subject in which the collagen matrix is implanted or applied. As non-limiting examples, in some embodiments, the collagen matrix is human and the subject is human, or the collagen matrix is equine and the subject is equine. In some embodiments, the collagen matrix is xenogeneic to the subject in which the collagen matrix is implanted or applied. As a non-limiting example, in some embodiments, the collagen matrix is porcine or bovine and the subject is human. In some embodiments, the collagen matrix is from a cadaveric donor.

In some embodiments, the collagen matrix has low immunogenicity or is non-immunogenic. In some embodiments, the collagen matrix is treated to reduce the immunogenicity of the matrix relative to a corresponding collagen matrix of the same type which has not been treated. Typically, to reduce immunogenicity the collagen matrix is treated to remove cellular membranes, nucleic acids, lipids, and cytoplasmic components, leaving intact a matrix comprising collagen and other components typically associated with the matrix, such as elastins, glycosaminoglycans, and proteoglycans. In some embodiments, immunogenicity of a treated collagen matrix is reduced by at least 50%, at least 60%, at least 70%, at least 80%, at least 90%, or more as compared to an untreated corresponding collagen matrix of the same type (e.g., treated dermis vs. untreated dermis). Any of a number of treatments can be used to reduce the immunogenicity of a collagen matrix, including but not limited to decellularization of the collagen matrix (e.g., by treatment with a surfactant and a protease or nuclease) or cellular disruption of the collagen matrix (e.g., by cryopreservation, freeze/thaw cycling, or radiation treatment). In some embodiments, the collagen matrix is decellularized by treatment with alkaline solution (dilute NaOH) followed by an acid treatment (dilute HCl), resulting in a decellularized neutralized substrate, which can then be submitted to serial washings to remove any remaining water soluble byproducts. Methods of decellularizing or disrupting the cells of a collagen matrix are described, for example, in U.S. Pat. Nos. 7,914,779; 7,595,377; 7,338,757; U.S. Publication No. 2005/0186286; Gilbert et al., *J. Surg Res* 152:135-139 (2009); and Gilbert et al., *Biomaterials* 19:3675-83 (2006), the contents of each of which is herein incorporated by reference in its entirety.

The reduction in immunogenicity can be quantified by measuring the reduction in the number of endogenous cells in the treated collagen matrix or by measuring the reduction in DNA content in the treated collagen matrix as compared to a corresponding untreated collagen matrix of the same type, according to methods known in the art. In one non-limiting method, reduction in immunogenicity is quantified by measuring the DNA content of the collagen matrix post-treatment. Briefly, a treated collagen matrix is stained with a fluorescent nucleic acid stain (e.g., PicoGreen® (Invitrogen) or Hoechst 33258 dye), then the amount of fluorescence is measured by fluorometer and compared to the amount of fluorescence observed in a corresponding untreated collagen matrix of the same type which has also been subjected to fluorescent nucleic acid stain. In another non-limiting method, reduction in immunogenicity is quantified by histological staining of the collagen matrix post-treatment using hematoxylin and eosin and optionally DAPI, and comparing the number of cells observed in the treated collagen matrix to the number of cells observed in a corresponding untreated collagen matrix of the same type which has also been subjected to histological staining.

In some embodiments, the collagen matrix that is seeded with a cell suspension is a flowable soft tissue matrix. For example, a collagen matrix can be prepared by obtaining a portion of soft tissue material, and cryofracturing the portion of soft tissue material, so as to provide a flowable soft tissue matrix composition upon thawing of the cryofractured tissue. Exemplary compositions and methods involving such flowable matrix materials are described in U.S. patent application Ser. No. 13/712,295, which issued as U.S. Pat. No. 9,162,011 on Oct. 20, 2015, the contents of which are incorporated herein by reference.

In some embodiments, the collagen matrix retains bioactive cytokines and/or bioactive growth factors that are endogenous to the collagen matrix. These bioactive cytokines and/or growth factors may enhance or accelerate soft tissue repair or regeneration, for example by recruiting cells to the site of the soft tissue injury, promoting extracellular matrix production, or regulating repair processes. In some embodiments, the collagen matrix retains one or more bioactive cytokines selected from interleukins (e.g., IL-1, IL-4, IL-6, IL-8, IL-15, IL-16, IL-18, and IL-28), tumor necrosis factor alpha (TNFα), and monocyte chemoattractant protein-1 (MCP-1). In some embodiments, the collagen matrix is skin and the one or more bioactive cytokines are selected from IL-4, IL-6, IL-15, IL-16, IL-18, and IL-28. In some embodiments, the collagen matrix is skin and the one or more bioactive cytokines are selected from IL-15 and IL-16. In some embodiments, the collagen matrix retains one or more bioactive growth factors selected from platelet-derived growth factor alpha (PDGFa), matrix metalloproteinase (MMP), transforming growth factor beta (TGFβ), vascular endothelial growth factor (VEGF), and epidermal growth factor (EGF). In some embodiments, the collagen matrix is skin and the one or more bioactive growth factors is PDGFa.

The retention of cytokines and/or growth factors by the collagen matrix, as well as marker profiles of which cytokines and/or growth factors are retained by the collagen matrix, can be determined according to methods known in the art, for example by immunoassay. A variety of immunoassay techniques can be used to detect the presence or level of cytokines and/or growth factors. The term immunoassay encompasses techniques including, without limitation, enzyme immunoassays (EIA) such as enzyme multiplied immunoassay technique (EMIT), enzyme-linked immunosorbent assay (ELISA), antigen capture ELISA, sandwich ELISA, IgM antibody capture ELISA (MAC ELISA), and microparticle enzyme immunoassay (META); capillary electrophoresis immunoassays (CEIA); radioimmunoassays (RIA); immunoradiometric assays (IRMA); fluorescence polarization immunoassays (FPIA); and chemiluminescence assays (CL). If desired, such immunoassays can be automated. Immunoassays can also be used in conjunction with laser induced fluorescence (see, e.g., Schmalzing and Nashabeh, *Electrophoresis*, 18:2184-2193 (1997); Bao, *J. Chromatogr. B. Biomed. Sci.*, 699:463-480 (1997)). Liposome immunoassays, such as flow-injection liposome immunoassays and liposome immunosensors, are also suitable for use in the present invention (see, e.g., Rongen et al., *J. Immunol. Methods*, 204:105-133 (1997)). In addition, nephelometry assays, in which the formation of protein/antibody complexes results in increased light scatter that is converted to a peak rate signal as a function of the marker concentration, are suitable for use in the present invention. Nephelometry assays are commercially available from Beckman Coulter (Brea, Calif.; Kit #449430) and can be performed using a Behring Nephelometer Analyzer (Fink et al., *J. Clin. Chem. Clin. Biol. Chem.*, 27:261-276 (1989)).

Antigen capture ELISA can be useful for determining the presence or level of cytokines and/or growth factors. For example, in an antigen capture ELISA, an antibody directed to an analyte of interest is bound to a solid phase and sample is added such that the analyte is bound by the antibody. After unbound proteins are removed by washing, the amount of bound analyte can be quantitated using, e.g., a radioimmunoassay (see, e.g., Harlow and Lane, Antibodies: A Laboratory Manual, Cold Spring Harbor Laboratory, New York, 1988)). Sandwich ELISA can also be used. For example, in a two-antibody sandwich assay, a first antibody is bound to a solid support, and the analyte of interest is allowed to bind to the first antibody. The amount of the analyte is quantitated by measuring the amount of a second antibody that binds the analyte. The antibodies can be immobilized onto a variety of solid supports, such as magnetic or chromatographic matrix particles, the surface of an assay plate (e.g., microtiter wells), pieces of a solid substrate material or membrane (e.g., plastic, nylon, paper), and the like. An assay strip can be prepared by coating the antibody or a plurality of antibodies in an array on a solid support. This strip can then be dipped into the test sample and processed quickly through washes and detection steps to generate a measurable signal, such as a colored spot.

Mesenchymal Stem Cells

The mesenchymal stem cells ("MSCs") which attach to the collagen matrix can be derived from any of a number of different tissues, including but not limited to adipose tissue, muscle tissue, birth tissue (e.g., amnion or amniotic fluid), skin tissue, bone tissue, or bone marrow tissue. The tissue may be harvested from a human subject or a non-human subject (e.g., a bovine, porcine, or equine subject). In some embodiments, the tissue is harvested from a human cadaveric donor. In some embodiments, the tissue is harvested from the subject who is to be treated for a soft tissue injury. In some embodiments, the tissue is allogeneic to the collagen matrix. As non-limiting examples, in some embodiments, the tissue is human and the collagen matrix is human, or the tissue is equine and the collagen matrix is equine. In some embodiments, the tissue is xenogeneic to the collagen matrix. As a non-limiting example, in some embodiments, the tissue is human and the collagen matrix is porcine or bovine. In some embodiments, the tissue and the collagen matrix are from the same donor (e.g., the same human donor, e.g., the same cadaveric donor). In some embodiments, the tissue and the collagen matrix are allogeneic but are harvested from different donors (e.g., different human donors, e.g., different cadaveric donors).

In some embodiments, mesenchymal stem cells that are seeded to or that attach to the collagen matrix are identified and characterized based on the presence or absence of one or more markers. In some embodiments, mesenchymal stem cells are identified as having a particular marker profile.

In some embodiments, the mesenchymal stem cells are characterized based on the presence or absence of one, two, three, four, or more markers of cell differentiation ("CD"). In some embodiments, the CD markers are selected from CD34, CD45, CD73, CD90, CD105, CD116, CD144, and CD166. Mesenchymal stem cell markers are described, for example, in Lin et al., *Histol. Histopathol.* 28:1109-1116 (2013), and in Halfon et al., *Stem Cells Dev.* 20:53-66 (2011).

As used herein, a "positive" mesenchymal stem cell marker is a marker on the surface of the cell (e.g., a surface antigen, protein, or receptor) that is unique to mesenchymal stem cells. In some embodiments, a positive mesenchymal stem cell marker is CD105, CD144, CD44, CD166, or CD90. In some embodiments, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, or more of the MSC cells seeded to the collagen matrix are positive for one or more of the CD markers CD105, CD144, CD44, CD166, or CD90.

As used herein, a "negative" mesenchymal stem cell marker is a marker on the surface of the cell (e.g., a surface antigen, protein, or receptor) that is distinctly not expressed by mesenchymal stem cells. In some embodiments, a negative mesenchymal stem cell marker is CD34 or CD116. In some embodiments, at least 25%, at least 30%, at least 35%, at least 40%, at least 45%, at least 50%, at least 55%, at least 60%, at least 65%, at least 70%, at least 75%, or more of the MSC cells seeded to the collagen matrix are negative for one or more of the CD markers CD34 and CD116. In some embodiments, the mesenchymal stem cells are identified as expressing one or more of the positive MSC markers CD105, CD144, CD44, CD166, or CD90 and are further identified as not expressing one or more of the negative MSC markers CD34 and CD116.

The presence and/or amount of a marker of interest on a mesenchymal stem cell can be determined according to any method of nucleic acid or protein expression known in the art. Nucleic acid may be detected using routine techniques such as northern analysis, reverse-transcriptase polymerase chain reaction (RT-PCR), microarrays, sequence analysis, or any other methods based on hybridization to a nucleic acid sequence that is complementary to a portion of the marker coding sequence (e.g., slot blot hybridization). Protein may be detected using routine antibody-based techniques, for example, immunoassays such as ELISA, Western blotting, flow cytometry, immunofluorescence, and immunohistochemistry. In some embodiments, the presence and/or amount of a marker of interest is determined by immunoassay (e.g., ELISA) as described above.

III. Methods of Making Compositions for Treating Soft Tissue Injuries

In another aspect, the present invention provides methods of making a composition for treating a soft tissue injury. In some embodiments, the method comprises:
(a) digesting a tissue to form a cell suspension comprising mesenchymal stem cells and non-mesenchymal stem cells;
(b) seeding the cell suspension onto a collagen matrix;
(c) incubating the collagen matrix seeded with the cell suspension under conditions suitable for adhering the mesenchymal stem cells to the collagen matrix; and
(d) removing the non-adherent cells from the collagen matrix.

In some embodiments, prior to step (b), the method further comprises treating the collagen matrix to reduce the immunogenicity of the collagen matrix.

Preparation of a Cell Suspension

A cell suspension comprising mesenchymal stem cells and non-mesenchymal stem cells for seeding onto the collagen matrix can be derived from a variety of types of tissues. In some embodiments, the tissue that is digested to form the cell suspension is selected from adipose tissue, muscle tissue, birth tissue (e.g., amnion or amniotic fluid), skin tissue, bone tissue, or bone marrow tissue. In some embodiments, the tissue is harvested from a human subject or a non-human subject (e.g., a bovine, porcine, or equine subject). In some embodiments, the tissue is harvested from a human cadaveric donor. In some embodiments, the tissue is harvested from the subject who is to be treated for a soft tissue injury.

Methods of forming a cell suspension from tissue and seeding the cell suspension onto a scaffold have been previously described for adipose tissue. See US 2010/0124776 and U.S. application Ser. No. 12/965,335, the contents of each of which are herein incorporated by reference in its entirety. A tissue is enyzmatically digested to form a cell suspension comprising mesenchymal stem cells and unwanted cells. In some embodiments, the tissue is digested with a collagenase solution (e.g., collagenase I). Optionally, the tissue is digested with the collagenase solution under continuous agitation (e.g., at about 75 rpm) for a suitable period of time (e.g., 30 minutes, 45 minutes, 60 minutes, or longer) until the tissue appears smooth by visual inspection.

Optionally, the tissue may be washed prior to or during digestion. In some embodiments, the tissue is washed with a volume of a solution (e.g., phosphate-buffered saline (PBS) S) or growth media) that is at least substantially equal to the tissue. In some embodiments, the tissue is washed with a solution comprising antibiotics (e.g., 1% penicillin and streptomycin) and/or antimycotics. In some embodiments, the tissue is washed at about 37° C., optionally with shaking to agitate the tissue. Washing may include repeated steps of washing the tissue, then aspirating off a supernatant tissue, then washing with fresh solution, until a clear infranatant solution is obtained.

Digestion of the tissue followed by centrifugation of the digested tissue results in the formation of a cell suspension, which can be aspirated to remove the supernatant and leave a cell pellet comprising mesenchymal stem cells and unwanted cells. The cell pellet is resuspended in a solution (e.g., growth media with antibiotics) and the resulting cell suspension is then seeded on a collagen matrix without any intervening steps of further culturing or proliferating the mesenchymal stem cell-containing cell suspension prior to the seeding step.

In some embodiments, the cell suspension can be enriched for stem cells by serial plating on a collagen-coated substrate prior to seeding the cell suspension on the collagen matrix. As one non-limiting example, muscle tissue can be prepared according to the following method to form an enriched cell suspension for seeding on a collagen matrix. The harvested muscle sample is minced, digested at 37° C. with 0.2% collagenase, trypsinized, filtered through 70 μm filters, and cultured in collagen-coated cell culture dishes (35-mm diameter, Corning, Corning, N.Y.) at 37° C. in F12 medium (Gibco, Paisley, UK), with 15% fetal bovine serum. After a suitable period of time (e.g., one hour), the supernatant is withdrawn from the cell culture dishes and replated in fresh collagen-coated cell culture dishes. The cells that adhere rapidly within this time period will be mostly unwanted cells (e.g., fibroblasts). When 30%-40% of the cells have adhered to each collagen-coated cell culture dish, serial replating of the supernatant is repeated. After 3-4 serial replatings, the culture medium is enriched with small, round cells, thus forming a stem cell-enriched cell suspension.

Seeding the Collagen Matrix

For seeding the cell suspension onto the collagen matrix, the collagen matrix may be placed in a culture dish, e.g., a 24-well culture plate and then the cell suspension added onto the collagen matrix. The collagen matrix onto which the cell suspension is seeded can be any collagen matrix as described herein. In some embodiments, the collagen matrix is skin, dermis, tendon, ligament, muscle, amnion, meniscus, small intestine submucosa, or bladder. In some embodiments, the collagen matrix is not articular cartilage. In some embodiments, wherein the collagen matrix comprises multiple layers, one or more of the matrix layers can be seeded with the cell suspension. As a non-limiting example, in some embodiments a dermal matrix comprises two layers, an epidermal facing basement membrane and a deeper hypodermal surface. The cell suspension can be seeded on the epidermal facing basement membrane, the deeper hypodermal surface, or both the epidermal facing basement membrane and the deeper hypodermal surface.

In some embodiments, the collagen matrix is treated to reduce immunogenicity prior to seeding the cell suspension on the collagen matrix. In some embodiments, the immunogenicity of the collagen matrix after treatment is reduced by at least 50%, at least 60%, at least 70%, at least 80%, at least 90%, or more as compared to an untreated corresponding collagen matrix of the same type. In some embodiments, the treated collagen matrix is non-immunogenic. As described above, any of a number of treatments can be used to reduce the immunogenicity of a collagen matrix, including but not limited to decellularization of the collagen matrix (e.g., by treatment with a surfactant and a protease or nuclease) or cellular disruption of the collagen matrix (e.g., by cryopreservation, freeze/thaw cycling, or radiation treatment). In some embodiments, the collagen matrix is treated with a decellularizing agent (e.g., a solution comprising a surfactant and a protease or a surfactant and a nuclease). Other suitable methods of decellularization are described in Crapo et al., *Biomaterials* 32:3233-43 (2011), the contents of which are incorporated by reference herein.

Following seeding of the cell suspension onto the collagen matrix, the cell suspension-seeded collagen matrix is incubated under conditions suitable for adhering mesenchymal stem cells to the matrix. In some embodiments, the cell suspension-seeded collagen matrix is incubated for several days (e.g., up to about 24 hours, about 36 hours, about 48 hours, about 60 hours, or about 72 hours) to allow adherence. In some embodiments, the cell suspension-seeded collagen matrix is incubated in a $CO_2$ incubator at about 37° C. The cell suspension-seeded collagen matrix may be incubated with culture medium (e.g., DMEM/F12), optionally with supplements and/or antibiotics and/or antimycotics (e.g., DMEM/F12 with 10% fetal bovine serum (FBS) and 1% penicillin, streptomycin, and amphotericin B (PSA)). In some embodiments, a greater number of mesenchymal stem cells adhere to the outward (epidermal) side or surface of the collagen matrix than to the inward (hypodermal) side or surface of the collagen matrix.

After the incubation step, the cell suspension-seeded collagen matrix is washed (e.g., with PBS or culture medium) to remove non-adherent cells from the collagen matrix. In some embodiments, the collagen matrix with adherent mesenchymal stem cells is placed in cryopreservation media (e.g., 10% DMSO, 90% serum) and kept frozen at −80° C.

Preparation of Tissues for Isolation of Cell Suspension

In some embodiments, the present invention provides techniques for manipulating large quantities or volumes of adipose, muscle, and other soft and fibrous tissues containing progenitor and stem cell populations, in a repeatable and consistent manner, by mechanical grinding to a defined particle size, in order to effectively prepare the tissues for isolation of a cell suspension (e.g., the stromal vascular fraction (SVF) of adipose tissue), prior to enzymatic or other digestion techniques.

Exemplary methods may include preparing large pieces and large quantities of adipose, muscle, or other tissues containing progenitor or stem cell populations, or both, for isolation of a cell suspension using a repeatable and consistent method of grinding, which can be applied to large-scale use. In this way, large pieces and large amounts of tissue can be efficiently broken down into a form suitable for subsequent isolation of the cell suspension using enzymatic or other digestion techniques. The use of mechanical grinding can enhance consistency and reproducibility through engineering controls.

In some instances, embodiments are directed toward the preparation of cadaveric tissues for optimal isolation of the cell suspension, in terms of large scale efficiency. Adipose or other tissue types are recovered from donor cadavers and transported to a processing facility. The tissue is repeatedly washed in Dulbecco's Phosphate-Buffered Saline (DPBS) or another isotonic reagent, optionally with antibiotic and/or antimycotic solution, to remove blood and other debris. The tissue is then ground from its original large size into small, consistent particles. The reduced particle size and increased surface area allow for more efficient digestion, by enzymes or other techniques, and improved yield of the progenitor and stem cell-containing cell suspension. The small particles can then be washed again in isotonic solution, such as DPBS.

In some embodiments, it may be useful to rinse the tissue, either before grinding, after grinding, or both. Specific rinsing protocols can be selected to achieve a desired result, and may be performed in any combination. For example, a final cell population may be affected by the number of rinses and the sequence in which the tissue is ground and rinsed. Therefore, embodiments of the present invention encompass techniques which involve rinsing before grinding, rinsing after grinding, and rinsing before and after grinding, and the selected technique may depend on the desired cell population.

The grinding protocols disclosed herein may provide enhanced results when compared to certain currently known techniques. For example, some known techniques involve enzymatically digesting large pieces of tissue, such as adipose tissue, in their originally harvested form. Relatedly, some known techniques are limited to the isolation of a cell suspension in only very small amounts (e.g., ~50 cc), for example using recovered lipoaspirate, whole pieces, or hand-minced particles.

In contrast, embodiments of the present invention facilitate large-scale manufacturing techniques using large amounts of tissue which can be processed in a timely and consistent manner. Toward this end, a mechanical grinder can be used to reduce harvested tissue into smaller particles to promote efficiency of isolation of a cell suspension for large scale manufacturing. In some aspects, such reduction of the particle size provides an increased surface area and allows quicker, more efficient digestion and isolation of the cell suspension. According to some embodiments, a mechanical grinder can be used to process the harvested tissue into particles having uniform sizes and shapes. In some embodiments, the process is automated so that tissue pieces having uniform size or shape properties can be obtained regardless of any subjectivity on the part of the operator.

In some embodiments, a standard grinder is used to reduce particle size consistently for large scale, regulated operations. Components of an exemplary grinding apparatus can be made of durable, autoclavable, and inert materials, such as stainless steel, which may facilitate ease of use and withstand large scale manufacturing workloads. In some cases, a grinding system can be manually operated. In some case, a grinding system can be electrically operated. The tissue types processed by the grinding system may include any soft tissues containing progenitor and stem cell populations such as adipose, muscle, skin, birth tissues, and the like. Various grinder speeds and attachments can be used to break down the tissue to a preferred particle size for each specific tissue type or application.

The tissue pre-processing systems and methods disclosed herein are well suited for use with the large scale production of tissue and medical devices involving large amounts of stem and progenitor cells. In accordance with these techniques, the donor cell yield can be maximized. In some cases, the grinding approaches can be utilized on the front end of the process, whereby soft/fibrous tissues are recovered from donor cadavers in bulk and ground at a processing facility to yield large amounts of cell suspensions comprising stem or progenitor cell populations. In some cases, tissue harvesting techniques may provide recovered tissue in large pieces and in large amounts. Relatedly, adipose processing techniques disclosed herein may be used as a primary method of large scale adipose recovery, which may optionally be supplanted by liposuction.

IV. Methods of Treatment

In yet another aspect, the present invention provides methods of treating a soft tissue injury in a subject using a composition as described herein (e.g., a composition comprising a collagen matrix and mesenchymal stem cells adhered to the collagen matrix). In some embodiments, the method comprises contacting a soft tissue injury site with a composition as described herein.

The compositions of the present invention can be used to treat subjects having any soft tissue injury that requires repair or regeneration. Such soft tissue injuries may result, for example, from disease, trauma, or failure of the tissue to develop normally. Examples of soft tissue injuries that can be treated according to the methods of the present invention include, but are not limited to, tears or ruptures of a soft tissue (e.g., tendon, ligament, meniscus, muscle, bladder or skin); hernias; skin wounds; burns; skin ulcers; surgical wounds; vascular disease (e.g., peripheral arterial disease, abdominal aortic aneurysm, carotid disease, and venous disease; vascular injury; improper vascular development); and muscle diseases (e.g., congenital myopathies; myasthenia gravis; inflammatory, neurogenic, and myogenic muscle diseases; and muscular dystrophies such as Duchenne muscular dystrophy, Becker muscular dystrophy, myotonic dystrophy, limb-girdle-muscular dystrophy, facioscapulohumeral muscular dystrophy, congenital muscular dystrophies, oculopharyngeal muscular dystrophy, distal muscular dystrophy, and Emery-Dreifuss muscular dystrophy). In some embodiments, the soft tissue injury is an injury to a tendon tissue, a ligament tissue, a meniscus tissue, a muscle tissue, a skin tissue, a bladder tissue, or a dermal tissue. In some embodiments, the soft tissue injury is a surgical wound, a trauma wound, a chronic wound, an acute wound, a deep channel wound, an exsanguinating site, or a burn.

In some embodiments, the composition is allogeneic to the subject that is being treated. As non-limiting examples, in some embodiments, the collagen matrix is human, the mesenchymal stem cells adhered to the matrix are human, and the subject is human; or the collagen matrix is equine, the mesenchymal stem cells adhered to the matrix are equine, and the subject is equine. In some embodiments, the composition is xenogeneic to the subject that is being treated. As a non-limiting example, in some embodiments, the collagen matrix is porcine or bovine, the mesenchymal stem cells adhered to the matrix are human, and the subject is human.

In some embodiments, the compositions described herein are used to treat humans having a soft tissue injury as described above. In some embodiments, the compositions described herein are used for veterinary applications. For example, in some embodiments, a composition of the present invention is used a non-human animal such as a non-human primate, mouse, rat, dog, cat, pig, sheep, cow, or horse having a soft tissue injury as described above. In some embodiments, a composition as described herein is used to treat a horse having a ruptured or torn soft tissue (e.g., ligament).

A mesenchymal stem cell-seeded collagen matrix of the present invention can be applied or introduced into a subject's body according to any method known in the art, including but not limited to implantation, injection, topical application, surgical attachment, or transplantation with other tissue. In some embodiments, the composition is administered topically. In some embodiments, the composition is administered by surgical implantation. The matrix may be configured to the shape and/or size of a tissue or organ or can be resized prior to administration (e.g., by a surgeon) to the size of the soft tissue injury being repaired. In some embodiments, a mesenchymal stem cell-seeded collagen matrix of the present invention is multilayered.

V. Examples

The following examples are offered to illustrate, but not to limit the claimed invention.

Example 1: Adherence and Survival of Adipose-Derived Stem Cells on Acellular Dermal Matrix Background Acellular dermal matrix samples were decellularized and washed in DPBS/10% PSA for 72 hours. Samples were placed in DPBS/4% PSA for 24 hours, and then placed in DPBS/1% PSA for 18 hours. Some samples to be used were placed in DMEM-F12/10% FBS/1% PSA while the rest of the tissue was stored in DPBS/4% PSA at 4° C.

Sample Preparation

First, the acellular dermal matrix samples were removed from antibiotic storage. Next, circular samples were cut to fit snugly into 24-well plate (diameter=15.6 mm) to avoid floating, while covering the entire well bottom. There were three rinsing groups: (a) DPBS stored samples, rinsed in DPBS/1% PSA; (b) DPBS stored samples, rinsed in DMEM-F12/20% FBS/1% PSA; and (c) Media stored samples, rinsed in DMEM-F12/20% FBS/1% PSA. For each rinsing group, samples were placed into 125 ml vented Erlenmeyer flask with 50 ml of either DPBS/1% PSA or DMEM-F12/20% FBS/1% PSA and shaken at 37° C. in horizontal shaker for 60 minutes at 100-125 RPM. Three rinses were performed, with the reagent changed at each rinse. The samples were then removed from the flask and placed in DMEM-F12/10% FBS/1% PSA (all Groups) in 24-well plate until seeding (>10 min). The plate layouts are shown below in Table 1 and Table 2.

TABLE 1

Plate 1 layout

| | Original Well | Rinse Well | Final Well | Controls |
|---|---|---|---|---|
| Group A | Top* 200,000 cells 1.8 ml total volume | 1.8 ml total volume | 1.8 ml total volume | Cells only 200,000 cells 1.8 ml total volume |
| | Bottom** 200,000 cells 1.8 ml total volume | 1.8 ml total volume | 1.8 ml total volume | Cells only 200,000 cells 1.8 ml total volume |
| Group B | Top* 200,000 cells 1.8 ml total volume | 1.8 ml total volume | 1.8 ml total volume | Media only (pre-inc) 1.8 ml total volume |
| | Bottom** 200,000 cells 1.8 ml total volume | 1.8 ml total volume | 1.8 ml total volume | Media only (post-inc) 1.8 ml total volume |
| Group C | Top* 200,000 cells 1.8 ml total volume | 1.8 ml total volume | 1.8 ml total volume | Top No cells 1.8 ml total volume |
| | Bottom** 200,000 cells 1.8 ml total volume | 1.8 ml total volume | 1.8 ml total volume | Bottom No cells 1.8 ml total volume |

*"Top" refers to the outward epidermal facing surface or basement membrane
**"Bottom" refers to the deeper dermal or hypodermal facing surface

TABLE 2

Plate 2 layout

| | Original Well | Rinse Well | Final Well | Controls |
|---|---|---|---|---|
| Group A | Top* 200,000 cells 1.8 ml total volume | 1.8 ml total volume | 1.8 ml total volume | Top No cells 1.8 ml total volume |
| | Bottom** 200,000 cells 1.8 ml total volume | 1.8 ml total volume | 1.8 ml total volume | |
| Group B | Top* 200,000 cells 1.8 ml total volume | 1.8 ml total volume | 1.8 ml total volume | Top No cells 1.8 ml total volume |
| | Bottom** 200,000 cells 1.8 ml total volume | 1.8 ml total volume | 1.8 ml total volume | |
| Group C | Top* 200,000 cells 1.8 ml total volume | 1.8 ml total volume | 1.8 ml total volume | Top No cells 1.8 ml total volume |
| | Bottom** 200,000 cells 1.8 ml total volume | 1.8 ml total volume | 1.8 ml total volume | Bottom No cells 1.8 ml total volume |

*"Top" refers to the outward epidermal facing surface or basement membrane
**"Bottom" refers to the deeper dermal or hypodermal facing surface Seeding Cultured adipose-derived stem cells (ASCs) were isolated by DPBS wash and TRYPLE™ Express detachment (cells used: 113712 (P1)). The cells were centrifuged and counted on Countess and diluted to $1.0 \times 10^6$ cells/ml. The media was aspirated from all sample wells, and 200,000 cells (200 μl) were added to each sample and positive control well. The volume of all wells was gently brought up to 1.8 ml with culture media (DMEM-F12/10% FBS/1% PSA). The samples were placed in a 37° C. $CO_2$ incubator for 42-48 hours.

Evaluation

For evaluating the samples, first the media was warmed to 37° C. and PRESTOBLUE™ to room temperature. The sample plates were removed from the incubator, then 1.81 media was added to each "Rinse" and "Final" well. With forceps, each graft was removed from the "Original" well and submerged 8-10 times in the "Rinse" well, then placed in the "Final" well, with appropriate orientation. For Plate 1 only, 200 µl of PRESTOBLUE™ reagent was added to each sample and control well. The samples were then incubated in the $CO_2$ incubator for 3 hours. Following incubation, seeded samples were removed to DPBS (-Ca/-Mg) in a new 12-well plate and placed in a shaker with low RPM. Triplicate aliquots were removed to black 96-well plate(s) for fluorescence reading, and the highest adherence samples (brightest readings) and no cell control were used for TRYPLE™ Express detachment and cell count. Plate 2 samples were then prepared for H&E histology using the highest adherence samples as seen from Plate 1.

Visual Assessment

Figure 1B:
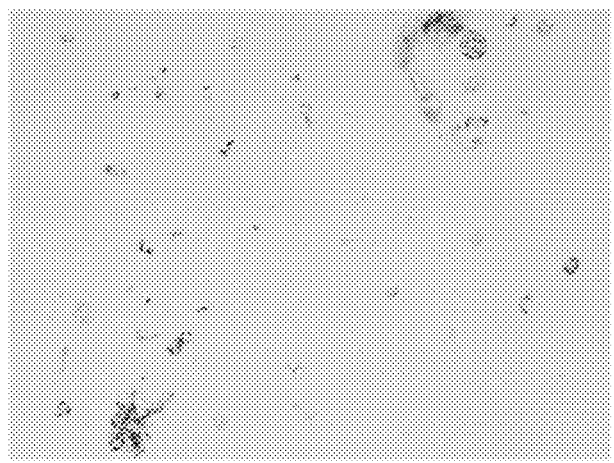
Figure 1C:
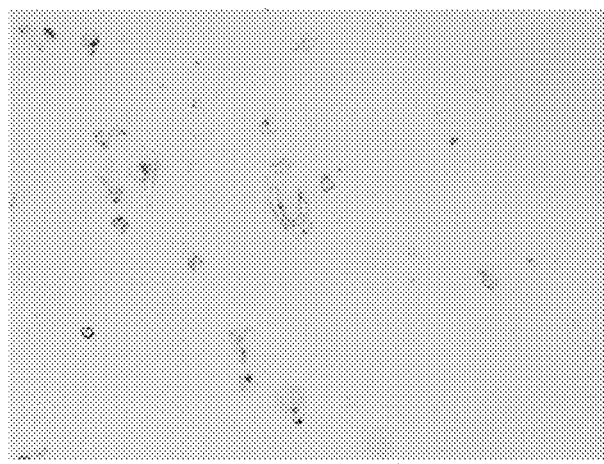

Each Original, Rinse, and Final well were viewed under inverted microscope (sample removed from Final), as shown in FIGS. 1A-1C. Group A and Group B wells were very similar for Top and Bottom samples. No live cells were visualized in any of the wells. For Group A, both top and bottom sample wells had the same general appearance, with the exception of the Top Rinse well, which had a noticeable amount of oily residue. The Group A Original and Rinse wells had small to medium amounts of dead cells and debris. The Final wells had slightly less dead cells and debris. The Group B wells were alike to Group A, with the exception of the Bottom original well, which had a noticeably larger amount of dead cells than the other wells in A or B.

Figure 2A:
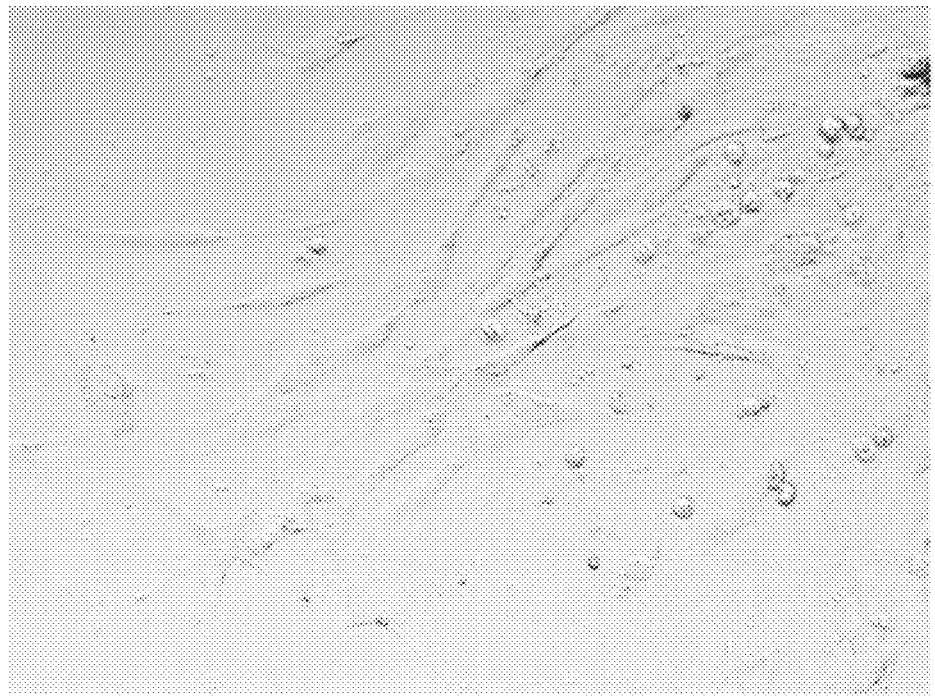
FIGS. 2A and 2B show Group C top original (A) and bottom original (B) wells having some live cells adhered to the plate.
Figure 2B:
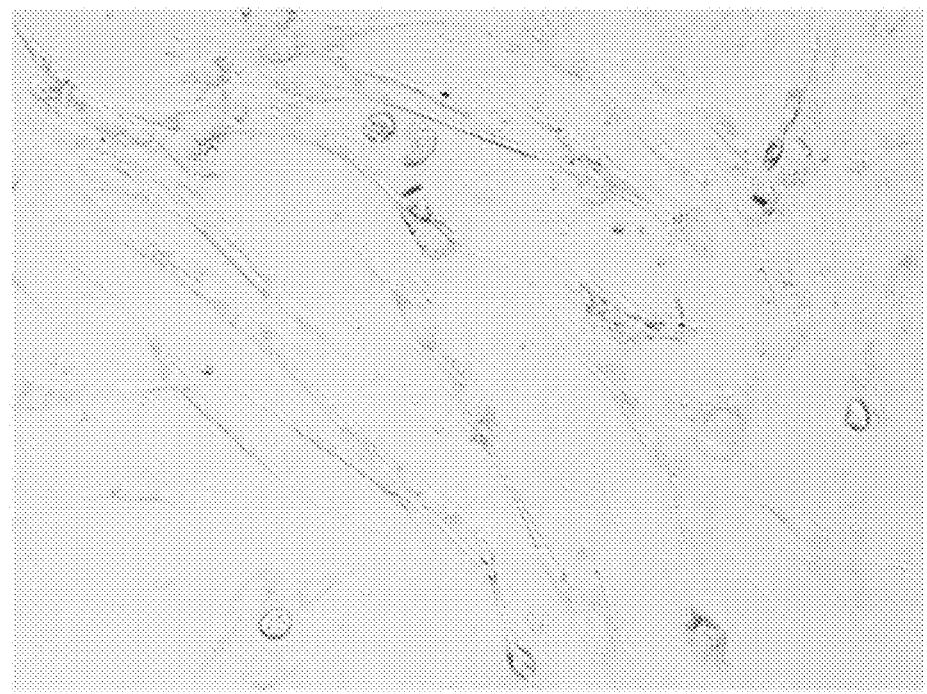
Figure 3:
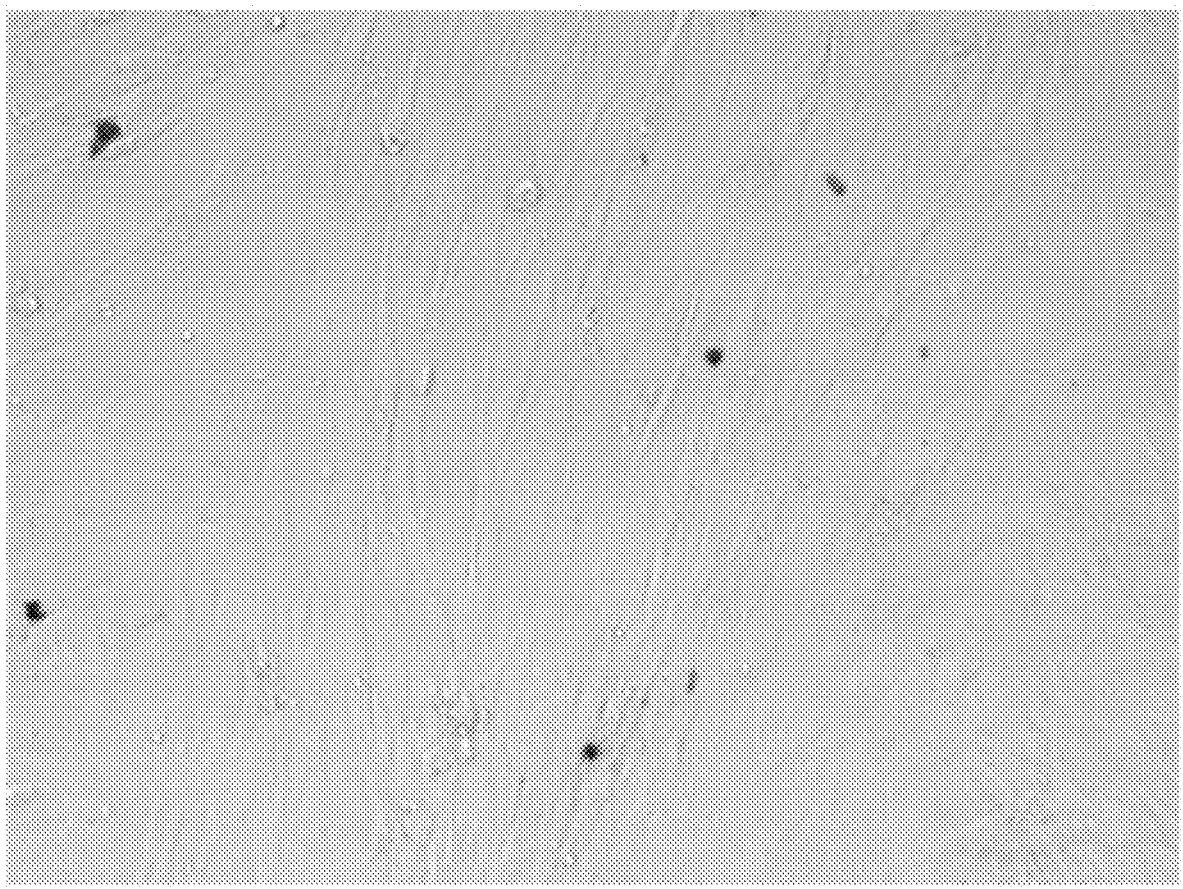
FIG. 3 shows cell only control wells showed elongated, healthy looking cells near confluence.

The Group C Rinse and Final wells were all similar to those in Groups A and B, showing medium amounts of dead cells and debris. However, the Group C Original wells were the only wells in any sample group to show live cells (FIGS. 2A-2B). The Top Original well had small amounts of floating dead cells in the middle with adhered living cells all around the rim. These cells likely poured over the edge of the graft and were able to adhere to the plastic during incubation. The Group C Bottom Original well also had live cells around the edges. The Bottom Original well had more visible cells than the top Original well, and this was expected because the sample had floated partially free from the plate, allowing cells to flow around. Both Group C Original wells also had medium amounts of dead cells throughout. The cell only control wells showed elongated, healthy looking cells near confluence (FIG. 3).

PRESTOBLUE™ Metabolic Assay

The percentage of metabolic activity was compared using the fluorescence (Table 3) and absorbance (Table 4) measurements from the PRESTOBLUE™ assay, and setting the cell-only positive control as the maximum possible level of activity. Media only backgrounds were subtracted from each sample well and positive control. Each sample was compared to the positive control, and the percent of metabolic activity for each well position was recorded. (The Group C Bottom sample partially floated free from the well plate, allowing cells to flow around and adhere to the plastic.)

TABLE 3

PRESTOBLUE™ Metabolic Assay based on fluorescence
Percentage of cells compared to control group
(Based on metabolic activity - PRESTOBLUE™ fluorescence)

|  | Original-seeded well | Rinse well | Final well-on skin |
| --- | --- | --- | --- |
| Group A Top | 4% | 1% | 46% |
| Group A Bottom | 4% | 0% | 25% |
| Group B Top | 5% | 2% | 60% |
| Group B Bottom | 4% | 0% | 28% |
| Group C Top | 5% | 2% | 65% |
| Group C Bottom | 59% | 1% | 45% |
| Unseeded samples | 4% |  |  |
| Cells only | 100% |  |  |

* The Group C Bottom sample partially floated free from the well plate, allowing cells to flow around and adhere to the plastic.

TABLE 4

PRESTOBLUE™ Metabolic Assay based on absorbance
Percentage of cells compared to control group
(Based on metabolic activity - PRESTOBLUE™ absorbance)

|  | Original-seeded well | Rinse well | Final well-on skin |
| --- | --- | --- | --- |
| Group A Top | −12% | 2% | 39% |
| Group A Bottom | −10% | 0% | 21% |
| Group B Top | −7% | 2% | 56% |
| Group B Bottom | −6% | 1% | 25% |
| Group C Top | −4% | 4% | 69% |
| Group C Bottom | 46% | 2% | 45% |
| Unseeded samples | 1% |  |  |
| Cells only | 100% |  |  |

* The Group C Bottom sample partially floated free from the well plate, allowing cells to flow around and adhere to the plastic.

Multiple trends were apparent in the metabolic activities. The Top surface of the skin showed higher metabolic activity using PRESTOBLUE™. The cells may more readily adhere to the Top than the Bottom or they may be more metabolically active after 48 hrs on the Top surface than on the Bottom.

Another trend was that the samples that were stored and rinsed in DMEM-F12/FBS had the highest metabolic activities and presumably the highest seeding efficiency. Although all Groups had a short soak in media immediately prior to seeding, the exposure to the serum-containing media was very different for the life of the samples. Those in Group C were stored in the media and rinsed in media prior to seeding. Samples from Groups A and B were stored in DPBS. Group A was rinsed in DPBS while Group B was rinsed in media.

TRYPLE™ Express Digestion

Figure 4A:
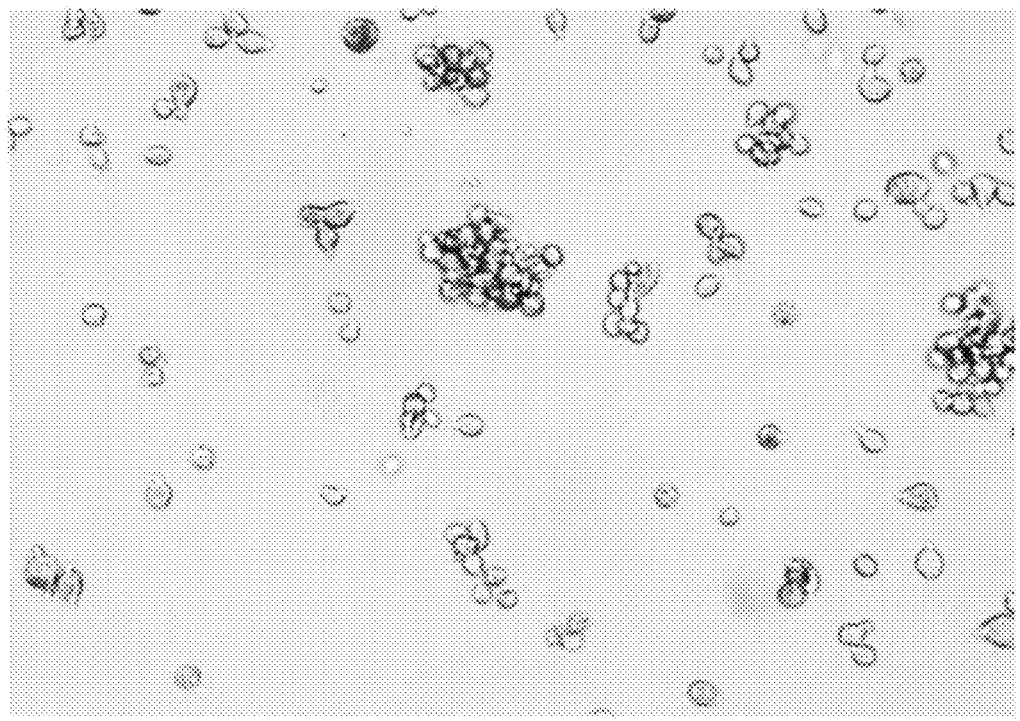
FIGS. 4A and 4B show recoverable cell populations from seeded samples.
Figure 4B:
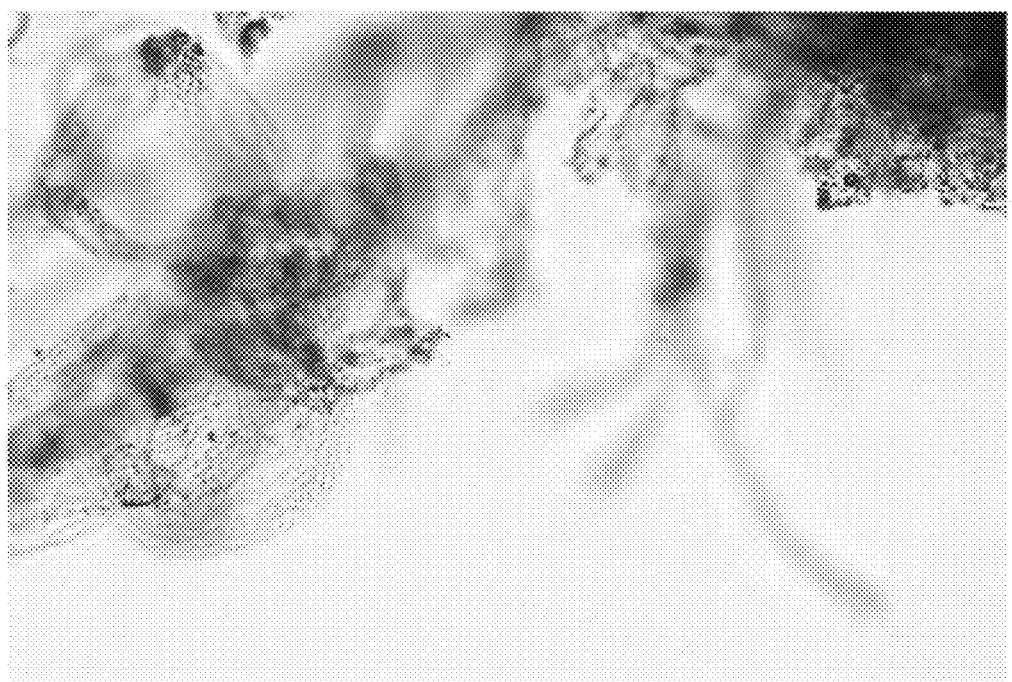

Following the PRESTOBLUE™ assay, samples from each group were washed in DPBS and cells were detached using TRYPLE™ Express. The cell populations were then centrifuged and re-plated in a 6-well plate. All seeded samples had recoverable cell populations, as viewed under the microscope. The Group C Top sample, which showed the highest level of metabolic activity, also showed the largest number of cells under the microscope, as shown in FIG. 4A. The Unseeded Sample (FIG. 4B) Did not Show any Cells Released.

Example 2: Preparation of Adipose Tissue for Forming a Cell Suspension

Background

Adipose for generating stem cells is typically recovered as lipoaspirate using a liposuction device. However, the liposuction process is tedious and rarely results in more than 1000 cc of adipose from a typical donor. Therefore, different recovery methods such as adipose en bloc by hand were investigated to maximize the amount of tissue recovered from a single donor. En bloc adipose could yield 2 L from a single donor, thus increasing the cell yields by a factor of 2. In this study, we compared the cell counts and cell phenotype of the cells recovered using both liposuction machine and en bloc adipose from the same donor.

Phase I: Method of Manipulation

The fibrous nature of the connective tissue within the en bloc adipose made simple manual manipulation impossible. It was determined that mechanical force was necessary for reducing particle size efficiently and consistently. The initial objective was to break down the large pieces of adipose into small particles to ensure efficient collagenase digestion.

Adipose en bloc was obtained from 2 donors and manipulated using various processing tools and food preparation devices in an attempt to prepare the tissue for collagenase digestion. The processing tools used were a meat grinder, an electric bone grinder, a meat tenderizer, a cheese grater, and a blender. The post-manipulation and post-digestion appearance of the adipose were recorded. The en bloc tissue was divided into groups and subjected to each form of manipulation. Those deemed successful at reducing particle size were then digested in collagenase and the cells were isolated.

The following methods of manipulation were successful based on ease of use, repeatability, physical appearance of manipulated adipose and resulting cell counts/viability on Countess: (1) electric bone grinder (EBG) with traditional particle set or small particle set; and (2) TSM #10 meat grinder, 3/8" and 3/16" pore size. In particular, the 3/8" pore size meat grinder gave an appearance much like lipoaspirate.

Phase II: Grinder and Tissue Washing Comparison

The manipulation of adipose en bloc was further tested, using the EBG with small particle set or prototype aggressive particle set as compared to the meat grinder using the 3/8" pore plate or the 3/16" pore plate. Additionally, procedures for rinsing the tissue were tested.

Adipose en bloc from an additional three donors was obtained and processed using variations of grinders and attachments as well as rinsing techniques to optimize viable cell numbers and best mimic lipoaspirate characteristics. Donor 3 was used to compare the meat grinder plate attachments (3/8" vs 3/16") and EBG with small particle set. Minimal variation between viable cell numbers in final pellets was found. Donor 4 was used to compare the meat grinder with 3/8" plate and EBG with aggressive particle set, using samples from each that were rinsed pre-grinding only or rinsed pre- and post-grinding. Donor 5 was used for a verification test with the same protocol as for Donor 4.

The 3/8" grinding plate was preferable due to ease of use and resulting similarity of the product to lipoaspirate particle size. Additionally, the speed and consistency of the meat grinder was superior to that of the EBG, although both grinders resulted in comparable numbers of viable cells. No conclusions could be drawn regarding rinsing pre-grinding only as compared to rinsing pre- and post-grinding.

Phase III: Adipose En Bloc Vs Lipoaspirate for Isolating Stromal Vascular Fraction The purpose of this study was to isolate a cell suspension (stromal vascular fraction, or SVF) from both en bloc and liposuction adipose from the same donor and utilize flow cytometry to characterize the cell populations obtained. The samples were processed in the following ways: (1) lipoaspiration; (2) adipose en bloc with 3/8" meat grinder plate and with pre-digestion rinse (pre-grinding and post-grinding); and (3) adipose en bloc with 3/8" meat grinder plate and no pre-digestion rinse (pre-grinding only). Adipose from five additional donors was recovered using both liposuction and en bloc from the same donor. Liposuction adipose was recovered from the abdominal area, while en bloc adipose was recovered from the abdominal area as well as the thighs. 200 cc samples for each pathway were processed in parallel. The lipoaspirate was processed according to standard protocols, which includes draining transport media followed by three DPBS rinses in a separatory funnel before digestion with collagenase.

The adipose en bloc followed two pathways prior to collagenase digestion, after which point standard protocols were used for processing. Prior to digestion, ~500 cc of the adipose en bloc was submerged in an equal volume of DPBS and poured back and forth between two beakers a total of six pours. This rinse was repeated for three total rinses. The adipose en bloc was then ground using the meat grinder and 3/8" plate. The ground adipose en bloc was then divided into two 200 cc samples. One sample was rinsed three times with DPBS in the separatory funnel prior to digestion while the other sample went straight to digestion after grinding. The en bloc pathway utilizing the extra rinse may slightly increase processing time compared to the lipoaspirate pathway. However, processing without the post-grinding rinse will decrease the overall processing time as compared to lipoaspirate.

The resulting SVF samples were analyzed by flow cytometry for various cell surface markers (CD 73, 90, 105, 34, 45, 271 and D&-Fib) to test for cell viability and positive and negative mesenchymal stem cell markers.

TABLE 5

Flow cytometry analysis of SVF samples

| | Lipoaspirate: avg cells/cc adipose* | Meat grinder en bloc + rinse: avg cells/cc adipose* | ANOVA p-value | Meat grinder en bloc, no rinse: avg cells/cc adipose* | ANOVA p-value |
| --- | --- | --- | --- | --- | --- |
| Total | 144,713 | 105,200 | 0.411 | 175,650 | 0.598 |
| Live | 118,604 | 77,257 | 0.300 | 133,394 | 0.780 |
| CD73 | 13,004 | 13,193 | 0.984 | 24,781 | 0.278 |
| CD90 | 100,542 | 53,120 | 0.252 | 107,087 | 0.904 |
| CD105 | 32,581 | 8,263 | 0.144 | 14,769 | 0.271 |
| CD271 | 4,410 | 5,257 | 0.836 | 9,052 | 0.273 |
| D7-FIB | 30,785 | 21,324 | 0.702 | 32,363 | 0.951 |
| CD34 | 84,272 | 36,494 | 0.135 | 66,446 | 0.596 |
| CD45 | 17,673 | 21,965 | 0.692 | 31,949 | 0.177 |

*n = 5

Figure 5:
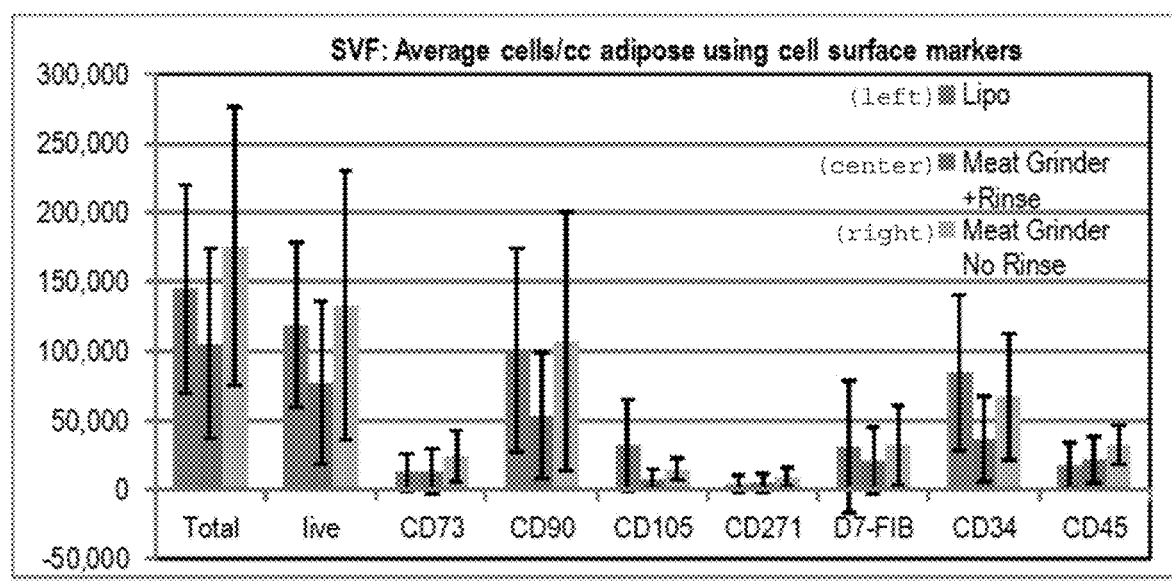
FIG. 5 shows comparison of average number of total and live cells, and number of cells positive for various CD markers, between the lipoaspirate, meat grinder+rinse, and meat grinder no rinse methods of isolating a stromal vascular fraction from adipose tissue.

Table 5 and FIG. 5 show that there was no significant difference of live and total cell counts between lipoaspirate and meat grinder en bloc+rinse or between lipoaspirate and meat grinder en bloc no rinse. Additionally, the surface markers were not significantly different.

There were no significant differences between Lipoaspirate and either of the Meat Grinder samples for any of the categories tested. The averages showed that the largest amount of total live cells came from the meat grinder no rinse method, as did the higher averages of CD73+ and CD90+. The highest averages of CD105+ were from the lipoaspirate method. CD34+ cells were very similar between the lipoaspirate and the meat grinder no rinse methods, while CD45+ was highest in the meat grinder no rinse method and lowest in the lipoaspirate method. The meat grinder+rinse samples showed mid-range or lowest amounts for all of the categories tested. We therefore chose the meat grinder with no rinse method as the method for processing en bloc adipose.

CONCLUSION

This study demonstrates a method of breaking down the en bloc adipose effectively for collagenase digestion. Our data also suggested that cell counts and cell phenotype per cc of adipose tissue were not significantly different between liposuction adipose and en bloc adipose. For liposuction, the volume of fat yielded per donor is 1 L, with an SVF yield/cc fat of 118,604 and a SVF yield/donor of 118 million. For en bloc processing, the volume of fat yielded per donor is 2 L, with an SVF yield/cc fat of 133,394 and a SVF yield/donor of 267 million. Therefore, en bloc adipose recovery is an effective means to increase the yield by increasing the total volume of adipose we can obtain per donor.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of making a composition for treating a soft tissue injury, the method comprising:
    (a) seeding a cell suspension onto a flowable acellular dermal collagen matrix, wherein the cell suspension comprises mesenchymal stem cells and non-mesenchymal stem cells, and wherein the flowable acellular dermal collagen matrix comprises cryofractured and thawed acellular dermal tissue having a disrupted extracellular matrix collagen or macrostructure and a partially disrupted collagen microfibrillar architecture;
    (b) incubating the flowable acellular dermal collagen matrix seeded with the cell suspension under conditions suitable for adhering the mesenchymal stem cells to the collagen matrix; and
    (c) removing non-adherent cells from the flowable acellular dermal collagen matrix.

2. The method of claim 1, wherein the flowable acellular dermal collagen matrix is obtained from a human donor, a porcine donor, a bovine donor, or an equine donor.

3. The method of claim 1, the method further comprising a step of processing a tissue to form the cell suspension of step (a).

4. The method of claim 3, wherein the tissue is selected from adipose tissue, muscle tissue, birth tissue, skin tissue, bone tissue, or bone marrow tissue.

5. The method of claim 3, wherein the tissue is adipose tissue.

6. The method of claim 3, wherein the tissue is lipoaspirate.

7. The method of claim 3, wherein processing the tissue to form the cell suspension comprises grinding the tissue to reduce tissue particle size.

8. The method of claim 3, wherein the cell suspension is a stromal vascular fraction.

9. The method of claim 3, wherein the flowable acellular dermal collagen matrix and the tissue are from a single donor.

10. The method of claim 3, wherein the flowable acellular dermal collagen matrix and the tissue are from a human donor.

11. The method of claim 3, wherein the flowable acellular dermal collagen matrix and the tissue are from a single human donor.

12. The method of claim 1, wherein the method further comprises treating the flowable acellular dermal collagen matrix to reduce immunogenicity prior to seeding the cell suspension onto the flowable acellular dermal collagen matrix.

13. The method of claim 12, wherein treating the flowable acellular dermal collagen matrix to reduce immunogenicity comprises removing one or more of cellular membranes, nucleic acids, lipids, and cytoplasmic components.

14. The method of claim 12, wherein the immunogenicity of the flowable acellular dermal collagen matrix after treatment is reduced by at least 50% relative to untreated flowable acellular dermal collagen matrix.

15. The method of claim 1, wherein the flowable acellular dermal collagen matrix seeded with the cell suspension is incubated for up to 24 hours at 37° C.

* * * * *